US006818012B2

(12) United States Patent
Ellingboe

(10) Patent No.: US 6,818,012 B2
(45) Date of Patent: Nov. 16, 2004

(54) PATIENT TEMPERATURE CONTROL SYSTEM WITH FLUID TEMPERATURE RESPONSE

(75) Inventor: Bruce Ellingboe, Littleton, CO (US)

(73) Assignee: Medivance, Incorporated, Louisville, CO (US)

( * ) Notice: Subject to any disclaimer, the term of this patent is extended or adjusted under 35 U.S.C. 154(b) by 77 days.

(21) Appl. No.: 10/233,843

(22) Filed: Sep. 3, 2002

(65) Prior Publication Data

US 2003/0114903 A1 Jun. 19, 2003

Related U.S. Application Data

(63) Continuation-in-part of application No. 09/976,197, filed on Oct. 11, 2001, now Pat. No. 6,699,267.

(51) Int. Cl.$^7$ .................................................. A61F 7/00
(52) U.S. Cl. ......................................... 607/104; 607/96
(58) Field of Search .................. 607/96, 104, 108–112; 219/494, 497

(56) References Cited

U.S. PATENT DOCUMENTS

| 3,007,473 A | 11/1961 | Jackson et al. |
| 3,064,649 A | 11/1962 | Fuson |
| 3,074,410 A | 1/1963 | Foster |
| 3,460,538 A | 8/1969 | Armstrong |
| 3,504,674 A | 4/1970 | Swenson et al. |
| 3,625,279 A | 12/1971 | Mayo |
| 3,888,259 A | 6/1975 | Miley |
| 3,995,621 A | 12/1976 | Fletcher et al. |
| 4,149,529 A | 4/1979 | Copeland et al. |
| T994,001 I4 | 5/1980 | Buckberg et al. |
| 4,259,961 A | 4/1981 | Hood, III |
| 4,416,280 A | 11/1983 | Carpenter et al. |
| 4,427,009 A | 1/1984 | Wells et al. |
| 4,459,468 A | 7/1984 | Bailey |
| 4,508,123 A | 4/1985 | Wyatt et al. |
| 4,512,163 A | 4/1985 | Wells et al. |
| 4,523,594 A | 6/1985 | Kuznetz |
| 4,691,762 A | * | 9/1987 | Elkins et al. .................. 165/46 |

(List continued on next page.)

Primary Examiner—Roy D. Gibson
(74) Attorney, Agent, or Firm—Marsh Fischmann & Breyfogle LLP

(57) ABSTRACT

An improved patient temperature exchange system and method is disclosed for use with one or more interconnectable patient contact pads. In one embodiment, the system includes a circulating pump for drawing fluid through the interconnected pad(s) under negative pressure, and for pumping the fluid through one of more heat exchange devices into a circulating reservoir. Also included in the system is a system controller specially configured for controlling the one or more heat exchange devices. The controller is further configured to employ one or more algorithms for adding and removing heat in a predetermined manner. One algorithm may include first and second control terms which provide for a theoretical heat transfer rate as well as instructions for changing temperature in an expedient manner while reducing isolations and overshoots. The system may be further configured with at least one alternate mode of operation for affecting water temperature when one or more water temperatures are outside a predetermined range.

32 Claims, 12 Drawing Sheets

U.S. PATENT DOCUMENTS

| | | | |
|---|---|---|---|
| 4,844,072 A | 7/1989 | French et al. |
| 4,962,761 A | 10/1990 | Golden |
| 4,966,145 A | 10/1990 | Kikumoto et al. |
| 5,051,562 A | 9/1991 | Bailey et al. |
| 5,097,829 A | 3/1992 | Quisenberry |
| 5,266,778 A | 11/1993 | Bailey |
| 5,270,005 A | 12/1993 | Raible |
| 5,332,884 A | 7/1994 | Bailey |
| 5,466,216 A | 11/1995 | Brown et al. |
| 5,573,502 A | 11/1996 | LeCocq et al. |
| 5,609,571 A | 3/1997 | Buckberg et al. |
| 5,609,620 A | 3/1997 | Daily |
| 5,634,940 A | 6/1997 | Panyard |
| 5,643,191 A | 7/1997 | Buckberg et al. |
| 5,645,531 A | 7/1997 | Thompson et al. |
| 5,702,358 A | 12/1997 | Witherspoon et al. |
| 5,730,720 A | 3/1998 | Sites et al. |
| 5,817,045 A | 10/1998 | Sever, Jr. |
| 5,862,675 A | 1/1999 | Scaringe et al. |
| 5,865,841 A | 2/1999 | Kolen et al. |
| 5,871,526 A | 2/1999 | Gibbs et al. |
| 5,895,418 A | 4/1999 | Saringer |
| 5,957,137 A | 9/1999 | Dalke et al. |
| 5,957,879 A | 9/1999 | Roberts et al. |
| RE36,386 E | 11/1999 | Abbott et al. |
| 5,997,816 A | 12/1999 | McIntosh et al. |
| 6,019,783 A | 2/2000 | Philips et al. |
| 6,033,432 A | 3/2000 | Augustine et al. |
| 6,042,559 A | 3/2000 | Dobak, III |
| 6,086,609 A | 7/2000 | Buckley |
| 6,095,992 A | 8/2000 | Augustine |
| 6,110,139 A | 8/2000 | Loubser |
| 6,149,674 A | 11/2000 | Borders |
| 6,197,045 B1 | 3/2001 | Carson |
| 6,254,626 B1 | 7/2001 | Dobak, III et al. |
| 6,261,312 B1 | 7/2001 | Dobak, III et al. |

\* cited by examiner

PATIENT TEMPERATURE CONTROL SYSTEM WITH FLUID TEMPERATURE RESPONSE

RELATED APPLICATIONS

This patent application is a continuation-in-part of U.S. patent application Ser. No. 09/976,197 filed on Oct. 11, 2001, now U.S. Pat. No. 6,699,267.

FIELD OF THE INVENTION

The present invention relates to a system and method for controlling the heat exchange function in a patient temperature control system and more particularly to controlling the heat exchange in a manner which avoids temperature overshoot and undue temperature oscillation.

BACKGROUND OF THE INVENTION

The use of contact pad systems for selectively cooling and/or heating bodily tissue is known. In such systems a fluid, e.g. water or air, is circulated through one or more pads to affect surface-to-surface thermal energy exchange with a patient. One highly effective contact pad and related system is disclosed in U.S. Pat. No. 6,197,045, hereby incorporated by reference in its entirety. As noted in the '045 patent, the ability to establish and maintain intimate pad-to-patient contact is often of key importance to fully realizing medical efficacies with contact pad systems.

In this later regard, the effect of temperature on the human body has been well documented. Elevated temperatures, or hyperthermia, may be harmful to the brain under normal conditions, and even more importantly, during periods of physical stress, such as illness or surgery. Conversely, lower body temperatures, or mild hypothermia, may offer some degree of neuroprotection. Moderate to severe hypothermia tends to be more detrimental to the body, particularly the cardiovascular system.

Temperature management, or thermoregulation, can be viewed in two different ways. The first aspect of temperature management includes treating abnormal body temperatures, i.e. cooling the body for elevated temperatures, or warming the body for lowered temperatures. The second aspect of thermoregulation is an evolving treatment that employs techniques that physically control a patient's temperature to provide a physiological benefit, such as cooling a stroke patient to gain some degree of neuroprotection.

Hypothermia may occur for a variety of reasons, including exposure to cold environments, brain injury, or complex surgical procedures. During surgery, a patient typically experiences mild hypothermia as a result of the effect of general anesthesia on the body's thermoregulatory system and prolonged exposure of internal organs. Mild hypothermia in the medical or the surgical patient has been thought to prolong the time to extubation, contribute to coagulopathies, increase the chance of infection, and increase cardiac demand as a result of shivering.

Hyperthermia may occur as a result of systemic inflammatory response, sepsis, stroke, or other brain injury. While the mechanism of the effect of the hyperthermia on the brain is not clearly understood, there is evidence to indicate that even mild increases in temperature may contribute to neurological deficits. Hyperthermia also increases the metabolic rate and may deplete energy stores in the body.

In view of the foregoing, it may be appreciated that recognized medical applications for contact pad systems are ever-increasing. By way of example, cooling pad systems may be utilized in early therapy to reduce neurological damage incurred by stroke and head trauma patients. Additional applications include selective patient heating/cooling during surgical procedures such as cardiopulmonary bypass operations.

As these and other medical applications have evolved, the present inventors have recognized the desirability of enhancing the predictability, responsivity, flexibility and portability of thermal exchange pad systems. More particularly, while known heating/cooling contact pad systems have proven effective for many applications, the present inventors have recognized that additional performance objectives and potential applications can be realized via the implementation of further improved control systems and associated control methodologies.

SUMMARY OF THE INVENTION

The inventors have recognized that it would be advantageous to configure a temperature control system which provides precise control of various heat exchange devices employed therein. The inventors have further recognized that the system may include a specially configured controller which employs various temperature control modeling which significantly reduces temperature oscillation and overshoot.

Described herein is a temperature controller for use in patient temperature control, system wherein the controller which is electrically connectable to a plurality of temperature sensors which monitors temperature at the inlet and outlet of the system and a flow meter which monitors flow rate of water to and from temperature control pads positionable on a patient for providing temperature control. Signals received at the controller indicate flow rate of fluid circulating through the system, the output temperature of the fluid circulating to at least one temperature control pad and the input temperature of fluid circulating from at least one temperature control pad.

During operations of the temperature control system, the controller is configured to process the received signals from the various sensors and calculate a number of control terms. The control terms are further employable to calculate one or more power signals which are transmittable to one or more heat exchange devices. The control terms may include first control term which is proportional to a first difference in temperature of fluid circulating in the system for fluid between the inlet temperature and selected set point. A second control term also employable by the controller may be proportional to a difference between the outlet temperature and a selected temperature set point. The system controller may further employ the first and second terms to generate a power signal which is transmittable to one or more of the heat exchange devices. In response, the heat exchange device may then affect temperature of the circulating fluid accordingly.

In one configuration of the invention, the heat exchange devices employable by the system may include a first heat exchange device specially configured for heating a fluid in response to a power signal. A second heat exchange device may be configured to cool the circulating fluid in response to receipt of the power signal. One or more auxiliary pumps may be employed for moving fluid past a heat exchange device.

In another configuration of the invention, the first control term may be modeled to be a theoretical heat transfer rate required to raise or lower the circulating water from the measured inlet temperature to a selected temperature set point. More particularly, the first control term may be calculated through a combination of a gain term, a measured flow rate, a provided flow offset, as well as the temperature difference described above.

The second control term may be specially configured to control the rate of change of temperature as the measured temperature at the outlet reaches the temperature set point. Specifically, issues that are addressed by the second term are oscillation and overshoots of the outlet temperature about a set point. According to another configuration of the invention, the second control term may be based on a modified proportional, integral, and derivative (PID) controller. Included as part of the PID control algorithm may be a modified integral and modified derivative terms. Also employable is a variable gain which is related to the measured flow rate of the fluid through the system.

With regards to the modified integral term, it may be approximated by a summation of measured errors over time. The error is the measured temperature difference between the outlet temperature and the temperature set point. The measured error may be employable in a controlled fashion. For example, a current error may be used in the summation if the error is decreasing too slowly or increasing at any rate. Integration may be further restricted such that the integral is not changed if the magnitude of the error is larger than a prescribed value. Minimum and maximum value of the integral term may be further limited so that it does not become to large a portion of the overall control of the temperature exchange devices.

With regards to the modified derivative term, this may be calculated through determining the slope of a "running least squares" line fit to the most recent N data points (errors). The magnitude of the modify derivative term may be also limited in certain situations to prevent response to noise.

According to the invention described herein, the system may be further configured to operate in one or more different modes depending on a measured temperature either at the inlet or outlet. For example, temperatures which are too high or too low may be dangerous to a patient. As such, the control model described herein may be configured to respond differently at certain temperatures. In one mode, if a temperature is detected to be too high, the modified integral term may be changed to increment at a faster rate. This may be done by multiplying the modified integral term by a weighting factor. Further, the modified derivative term may be disabled if the temperature is dropping.

According to the invention described herein the controller may be configured as part of a temperature control system. The temperature control system may include one or more temperature sensors which monitor temperature at the inlet and outlet of the system. The outlet temperature sensor is specially configured to measure temperature of water flowing from any reservoir within the system to temperature control pads which are positionable on a patient. The inlet temperature sensor measures fluid temperature flowing from the temperature control pads to the system described herein. The system may further include one or more reservoirs for holding the circulating fluid and one or more pumps for circulating the fluid through the system at a selected rate. Further included in the system may be at least one auxiliary pump configured for pumping the fluid through the first or second heat exchangers to affect the heat exchange between the medium located in the heat exchanger and fluid. Depending on the system configuration, the rate of fluid flow through the auxiliary pump may be the means of controlling temperature. Further in connection with the controller may be a user interface device, through which a system user may manually enter values to be employed by the system such as temperature set points and minimum and maximum temperatures. Programmed sequences for controlling temperature may also be entered. For example, during surgery, controlled cooling or heating may be employed during different parts of the procedure. These sequences may be preprogrammed such that they may be automatically or manually initiated.

With regards to system operation, the temperature control pads may be connected to the temperature control system and a temperature control set point identified prior to performance of a surgical procedure. Once the procedure is begun and the temperature control system is initiated, periodic readings are taken at the inlet and outlet temperature sensors as well as from the flow meter. For each of these periodic readings, values for the first and second control terms are calculated. As was discussed above, first control term is proportional to a measured error at the temperature inlet between the measured fluid temperature and the set point. The second control term is proportional to an error between the outlet temperature and the set point.

Once the first and second control terms are calculated a power signal is generated and transmitted to the heat exchange device identified to provide the desired type of heat exchange. As the temperatures are being monitored it may be detected that the measured temperatures in either the outlet or inlet exceeds a specified range of temperatures. In this situation, the controller automatically initiates an alternative mode of operation wherein the second term is incremented at a faster rate. Once the temperature begins moving in the direction of an acceptable range, the derivative term may be set to zero so as not to slow the adjustment process. Incrementing the second term at a faster rate is continued until it is detected that the outlet temperature is back within the desired range. At this point the controller may initiate the normal mode of operation. During operation, as part of a pre-programmed sequence, one or more temperature set points may be identified whereby the system alters the fluid temperature to the desired temperature set point.

DETAILED DESCRIPTION

FIGS. 1, 2 and 3A–3C relate to one embodiment of a patient temperature control system comprising numerous aspects of the present invention. As will be apparent to those skilled in the art, such aspects may be implemented in various other embodiments.

Figure 1:
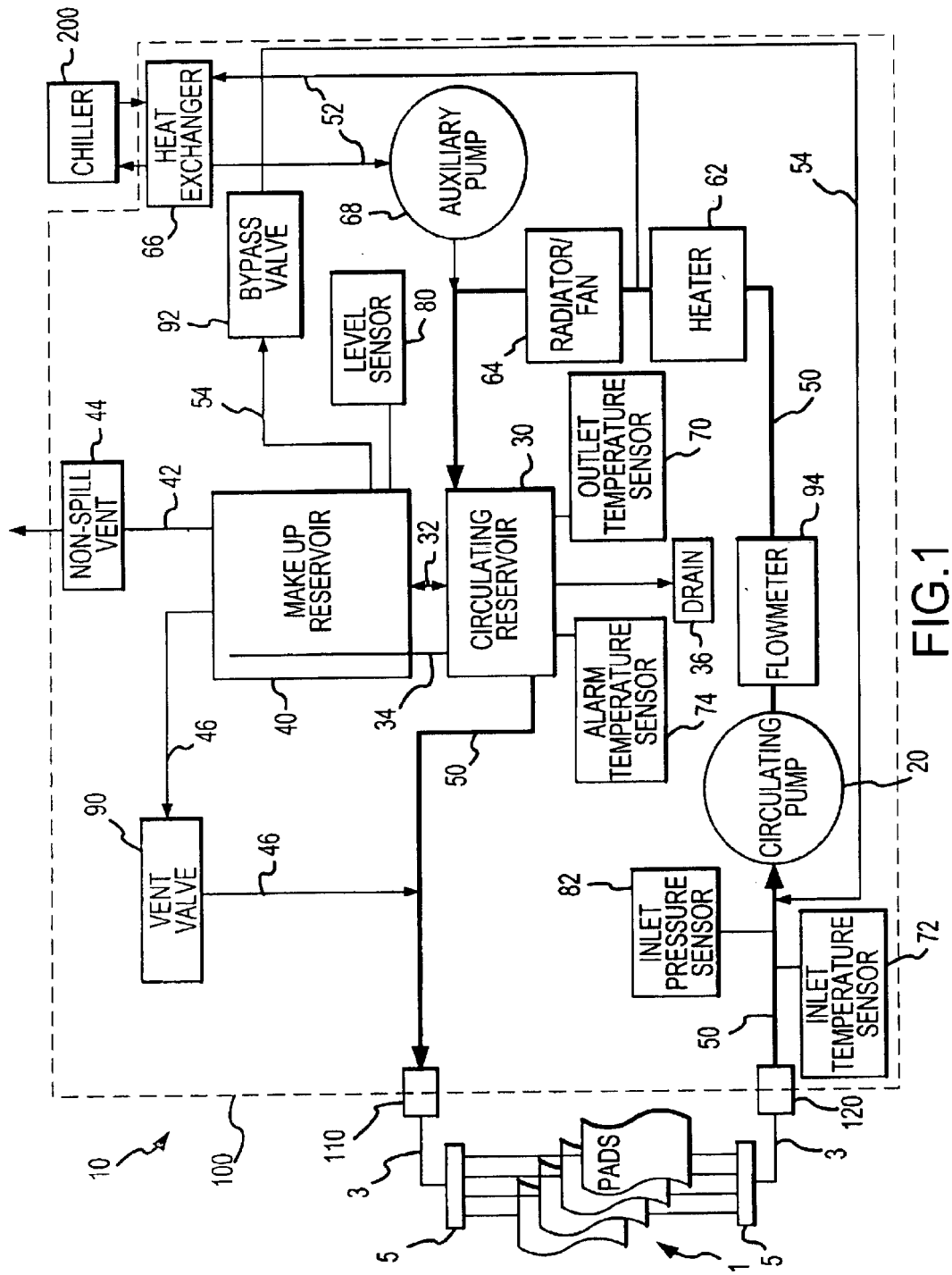
FIG. 1 is a hydraulic schematic of one embodiment of a patient temperature control system comprising numerous aspects of the present invention.

In accordance with the hydraulic schematic of FIG. 1, the illustrated patient temperature control system 10 may be selectively interconnected to one or more contact pad(s) 1 for heating/cooling a patient. By way of example, pad(s) 1 may be of a type described in U.S. Pat. No. 6,197,045. The system 10 includes a circulating pump 20 for drawing fluid (e.g. water) through the pad(s) 1 under negative pressure (e.g. preferably at least about −3 psi, and negative most preferably at least about −7 psi, during normal operations), a circulating reservoir 30 and make-up reservoir 40 for containing fluid, and controllable heat exchange devices 62, 64 (e.g., an electric heater for fluid heating and a radiator/fan temperature fluid cooling) for heating/cooling fluid circulated through the system 10.

A main fluid line 50 (e.g., defined by tubing lines) fluidly interconnects the noted system componentry. A secondary fluid line 52 (e.g., defined by tubing lines) may be fluidly interconnected at each end to the main fluid line 50 with an in-line heat exchange device 66 to effect further selective fluid cooling/heating via an external interface. Additionally, a fluid bypass line 54 (e.g. defined by tubing lines) may be fluidly interconnected between reservoir 40 and circulating pump 20 for selective fluid conditioning purposes.

Reservoirs 30 and 40, circulating pump 20, heat exchange devices 62, 64 and 66, and the noted fluid lines 50, 52 and 54, all may be located within a common housing 100. Housing 100 may be provided with a selectively openable/closeable fluid output port 110 and fluid input port 120 for selective fluid interconnection of the pad(s) 1 therebetween. In the latter regard, opposing tubing 3/manifold 5 assemblies may be provided for interconnection to the outlet port 110 and inlet port 120, with one or more pad(s) 1 fluidly interconnectable between the opposing manifolds 5.

As will be further described, during filling/emptying of the pad(s) 1 (e.g. after fluid conditioning and interconnection of the pad(s) 1), fluid flows from the circulating reservoir 30 into the pad(s) 1 and from/to make-up reservoir 40 to/from circulating reservoir 30. During normal patient heating/cooling operations, fluid is circulated through the circulating reservoir 30, pad(s) 1, and heat exchange devices 62 and 64 and/or 66, substantially free from passage through the make-up reservoir 40.

The fluid containment, handling and heat exchange componentry of system 10 will now be described in further detail with reference to FIGS. 1 and 3A–3C. Circulating reservoir 30 may be physically located below the make-up reservoir 40, with a fluid interconnection line 32 extending therebetween. In the embodiment shown in FIGS. 3A–3C, the top of the circulating reservoir 30 is located below the bottom of the make-up reservoir 40. As will become apparent, such an arrangement provides for the gravity flow of fluid flow from make-up reservoir 40 into circulating reservoir 30. Relatedly make-up reservoir 40 may be physically located lower than pad(s) 1 when interconnected.

During operation, gas within circulating reservoir 30 may rise through fluid interconnection line 32 into the make-up reservoir 40. Further, a vent line 34 may be provided at the top of circulating reservoir 30 for gas removal therefrom. Vent line 34 may be vented through a non-spill outlet to the atmosphere or, as shown in FIG. 1, may be vented into the make-up reservoir 40. In turn, make-up reservoir 40 may be provided with a vent line 42 having a non-spill outlet 44 to the atmosphere. Vent 44 functions to maintain atmospheric pressure (e.g. about 14.7 psi) within the make-up reservoir 40. By way of example, vent 44 may comprise a porous hydrophobic membrane that restricts fluid flow and permits gas passage therethrough.

As may be appreciated, the inclusion of vent lines 34 and 42 advantageously provides for the removal of gaseous bubbles from the fluid circulated through pad(s) 1. In this regard, it should be noted that if a leak develops in the fluid circuit located outside of system 10 (e.g., a leak in the pad(s) 1), air will be drawn through the leak into the system 10 due to the negative pressure operating condition generated by circulating pump 20. In turn, such air will ultimately be exhausted from make-up reservoir 40 via the non-spill vent 44.

For purposes of emptying fluid from the pad(s) 1, the system 10 may include a vent line 46 interconnected at one end to the main fluid line 50 downstream of the circulating reservoir 30. The other end of vent line 46 may be interconnected to the top of make-up reservoir 40. A controllable vent valve 90 may be interposed along the vent line 46 at a physical location above the make-up reservoir 40 to provide for selective gas flow therethrough. More particularly, to empty the pad(s) 1, vent valve 90 may be selectively opened while circulating pump 20 is operating. In turn, air will be drawn through the vent 44, make-up reservoir 40, and vent valve 90 into the main fluid line 50 for passage through and purging of fluid within the pad(s) 1. At the same time, the fluid within the pad(s) 1 will be drawn therefrom by circulating pump 20 and thereafter collected in the make-up reservoir 40 via passage through the circulating reservoir 30.

Fluid may be removed from the system 10 via a drain 36 fluidly interconnected to and located below the circulating reservoir 30. When the pad(s) 1 are disconnected from the system 10, fluid may be readily introduced into the system 10 via the outlet port 110.

The heat exchange devices 62, 64 and 66 may all be located downstream of the circulating pump 20 and upstream of the circulating reservoir 30. Such positioning isolates the pressure drop associated with these components to the positive pressure side of circulating pump 20, thereby enhancing the ability of pump 20 to maintain the desired negative pressure within the pad(s) 1.

As further illustrated in FIG. 1, a separately controllable auxiliary pump 68 may be interposed along the secondary fluid line 52 for selectively circulating fluid through the heat exchange device 66. The heat exchanger device 66 may be disposed at a location within housing 100 that facilitates convenient interconnection with an external cooling and/or heating source. In one arrangement, the heat exchange device 66 may comprise a two-sided exchanger located in the bottom of housing 100, wherein fluid is circulated from an external chiller 200 through one side of the heat exchanger 66 and back through the chiller 200, wherein fluid within system 10 is passed through the other side of the heat exchanger 66 for enhanced cooling purposes. The speed of auxiliary pump 68 may be selectively controlled to affect the desired degree of fluid cooling/heating at exchanger 66. The provision of a secondary fluid line 52 as described above allows large and heavy refrigeration or heating equipment to be utilized in combination with system 10, yet be physically separated from system 10. This results in a significantly smaller and lighter system 10, enhancing portability.

With further respect to fluid bypass line 54, FIG. 1 shows the fluid interconnection thereof between make-up reservoir 40 and main fluid line 50 at a location upstream of circulating pump 20 and downstream from the pad(s) 1. The fluid bypass line 54 is routed through a controllable bypass valve 92, wherein fluid flow through the fluid bypass line 54 may be selectively controlled. In particular, bypass valve 92 may be opened to provide for the preconditioning of fluid in the system 10 prior to interconnection of the pad(s) 1. For example, fluid may be circulated through the bypass fluid line 54 via operation of circulating pump 20 and heat exchange devices 62, 64 and/or 66, thereby achieving the desired fluid temperature prior to interconnection of the pad(s) 1. In turn, effective patient temperature control can be more rapidly established and patient comfort may be enhanced.

In addition to the above-described fluid routing, containment and heat exchange componentry, the system 10 illustrated in FIGS. 1, 2 and 3A–3C also comprises a number of sensors for system control and enhanced performance purposes. In particular, a level sensor 80 may be provided at make-up reservoir 40 for sensing the amount of fluid therewithin. In one arrangement, level sensor 80 may comprise a pressure sensor, wherein the amount of fluid within reservoir 40 may be determined in relation to the sensed head pressure. Such fluid level sensing may be employed in system 10 to provide for user alert, system control and/or system disablement upon sensing of fluid levels below and/or above predetermined amounts.

For purposes of establishing the desired temperature of fluid circulated through the pad(s) 1, system 10 may utilize one or more temperature sensors. In particular, an outlet temperature sensor 70 may be located along the main fluid line 50 at a location downstream of the heat exchange devices 62, 64 and 66. In the embodiment illustrated in FIG. 1, the outlet temperature sensor 70 is provided at the circulating reservoir 30 for sensing the fluid temperature therewithin. Alternatively and/or additionally, an inlet temperature sensor 72 may be located along the main fluid line 50 at a location downstream of the pad(s) 1 and upstream from the heat exchange devices 62, 64 and 66. In the embodiment illustrated in FIG. 1, the inlet temperature sensor 72 is located upstream from the circulating pump 20. The fluid temperature sensed by sensors 70 and/or 72 may be utilized in connection with the control of one or more of the heat exchange devices 62, 64 and 66 (e.g. by controlling operation of auxiliary pump 68), to obtain the desired temperature for fluid circulation. As will be further described, the inclusion of both an outlet fluid temperature sensor 70 and inlet temperature sensor 72 advantageously allows for the ongoing computation of the rate of thermal energy exchange between the pad(s) 1 and a given patient, thereby yielding information employable for enhanced system performance. (e.g. control of the heat exchange devices 62, 64 and pump 68 to rapidly ramp to within a predetermined range of a "targeted" patient temperature).

In addition to temperature sensors 70 and 72, system 10 may further include an alarm fluid temperature sensor 74 located along the main fluid line 50 downstream from the heat exchange devices 62, 64, and 66. In the embodiment illustrated in FIG. 1, the alarm temperature sensor 74 is located at the circulating reservoir 30 for sensing the fluid temperature therewithin. The alarm temperature sensor 74 provides for temperature sensing that may be redundant to that of outlet temperature sensor 70, wherein any risk of circulating fluid outside of a predetermined temperature range may be substantially reduced. For example, system 10 may be provided so that upon the sensing of a fluid temperature outside of a predetermined high/low range, by either of the sensors 70 or 74, circulating pump 20 is automatically stopped.

System 10 may further include an inlet pressure sensor 82 located downstream of the interconnectable pad(s) 1 and upstream of the circulating pump 20. More particularly, the inlet pressure sensor 82 may be located along the main fluid line 50 between the inlet port 120 and inlet side of circulating pump 20. The sensing of fluid pressure at the noted location facilitates the maintenance of a predetermined, desired negative pressure within the interconnectable pad(s) 1. In this regard, the speed of the circulating pump 20 may be controlled in relation to the sensed fluid pressure at sensor 82. Such functionality is provided by the described arrangement regardless of whether one or a plurality of pad(s) 1 are interconnected to the system 10.

System 10 may also include a flow meter 94 located along the main fluid line 50 downstream of circulating pump 20. In the illustrated embodiment, the flow meter 94 is located between the circulating pump 20 and heat exchange devices 62, 64 and 66. The flow meter 94 provides for the sensing of fluid flow through the main fluid line 50, thereby facilitating the monitoring of expected versus actual fluid flow through the pad(s) 1. In turn, such functionality allows system 10 to detect potential, undesired fluid flow obstructions (e.g., kinks in the tubing lines 3 interconnecting the pad(s) 1 to the inlet port 110 or outlet port 120). Additionally, the monitoring of fluid flow rates facilitates the determination of patient thermal energy exchange and fluid heating/cooling control.

As indicated above, the various heat exchange devices 62, 64 and 66, pumps 20 and 68, and valves 90 and 92 may all be selectively controlled. As also noted, the identified sensors may provide information employable to achieve a number of system control functions. To further describe such functionalities, specific reference will now be made to the electrical schematic of FIG. 2. Of importance, system 10 may include at least one controller, or microprocessor 130, operably interconnected to the various noted sensors via a signal-conditioning interface 140. By way of example, the signal conditioning interface 140 may comprise hardware/software for filtering, shifting, etc. of analog signals received from the various sensors. Further, an A/D converter may be provided at interface 140 or processor 130 to convert the conditioned signals into digital signals for processing.

As will be appreciated, the processor 130 may be preprogrammed to process the digital signals to provide the various control functionalities discussed herein. More particularly, the processor 130 may utilize control algorithms and associated preset/user-defined control limits/ranges stored in a memory 132 (e.g., a non-volatile random access memory). For purposes of selectively modifying certain control limit sets employable with the control algorithms, as well as initiating/terminating certain system operations, system 10 may include a user interface 150 interconnected with processor 130. The user interface 150 may include one or more input devices (e.g., a keypad entry, touch screen, mouse with a pointer, etc.), as well as one or more displays 152. The displays 152 may display system operating conditions, settings and alarms to a user and/or prompt a user in the set-up and operation of system 10, as well as remedial actions that may be undertaken in the event of a detected system condition of concern.

At this point, it should be noted that system 10 may further include or be interconnectable with a power source 160 (e.g., 24-volt DC source) that powers an internal drive circuit (not shown). In turn, the drive circuit may supply drive signals to the various sensors noted above, as well as a temperature simulator 180, calibration simulator 182 and control chip 172. Additionally, power source 160 may provide drive signals via a switch 162 to the vent valve 90, bypass valve 92, circulating pump 20, and auxiliary pump 68, and to heater 62 via a solid state relay 164 (SSR). Finally, power source 160 may provide drive signals directly to radiator/fan 64 and an electronics fan 170.

While power source 160 supplies drive signals to each of the above-noted fluid handling and heat exchange devices, processor 130 controls the operation thereof. More particularly, processor 130 may control the open/close state of vent valve 90 and bypass valve 92. Processor 130 may also control the operation (e.g., the speed) of circulating pump 20 and auxiliary pump 68. Further, processor 130 can control the operation of heater 62 and radiator/fan 64 (e.g., via control of the fan) to effect the desired amount of heating and cooling. In the embodiment shown in FIG. 2, a relay 166 is interposed between the processor 130 and auxiliary pump 68 and radiator/fan 64, wherein control signals from processor 130 will be directed to radiator/fan 64 when an external heat exchange device 200 is not utilized, and wherein control signals from processor 130 are directed to auxiliary pump 68 when an external heat exchange device 200 is interconnected. In other arrangements, control signals may be provided in tandem to both radiator/fan 64 and auxiliary pump 68 for dual operation thereof.

Figure 2:
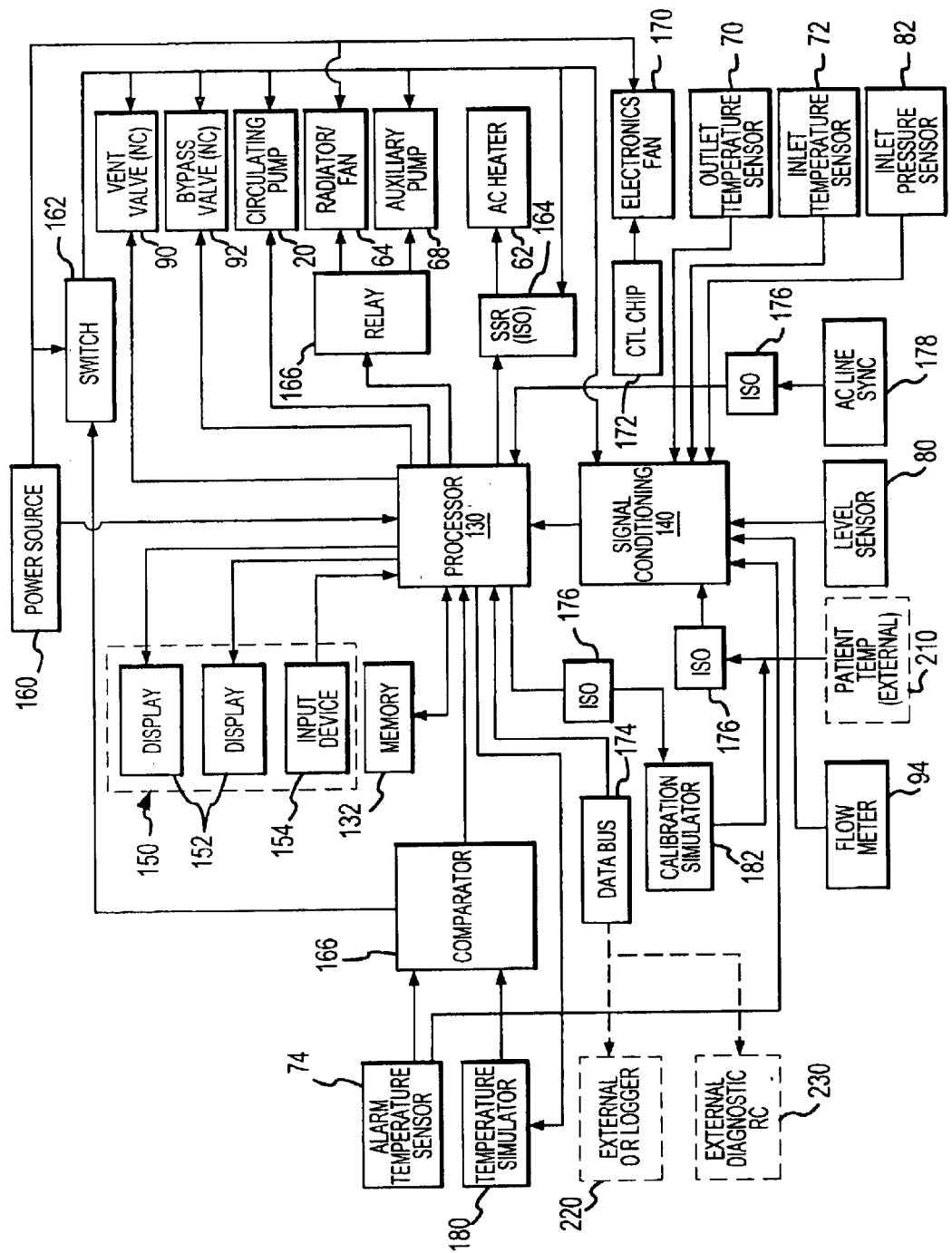
FIG. 2 is an electrical schematic corresponding with the embodiment of FIG. 1.
Figure 3A:
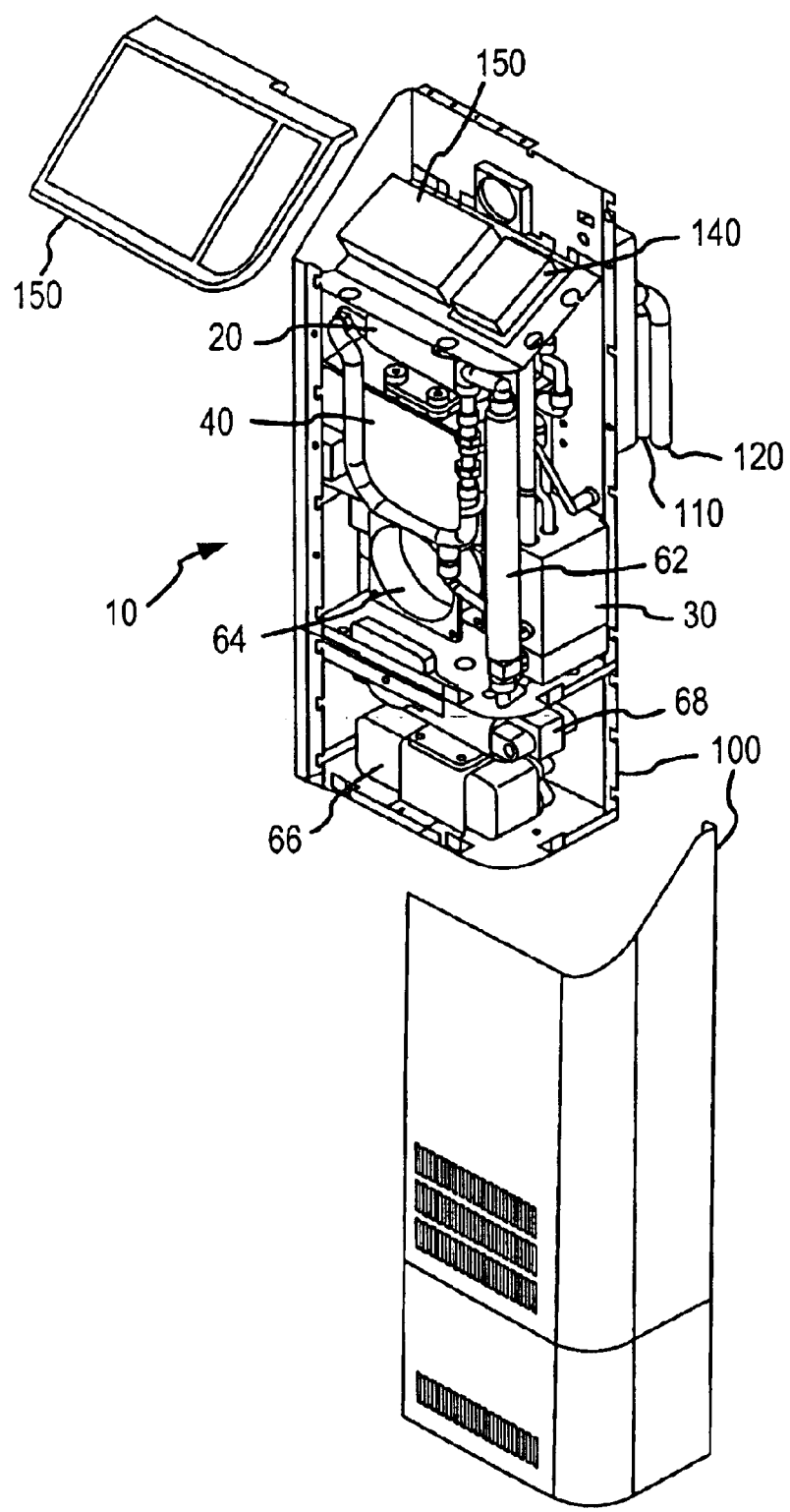
FIGS. 3A, 3B and 3C are an exploded perspective view, a front view and a side view, respectively, of the embodiment of FIG. 1.
Figure 3B:
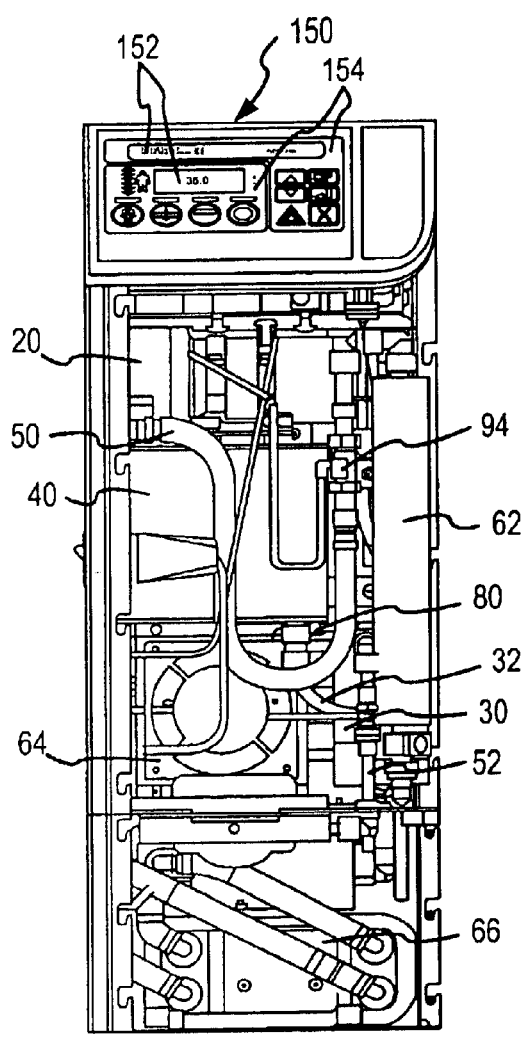
Figure 3C:
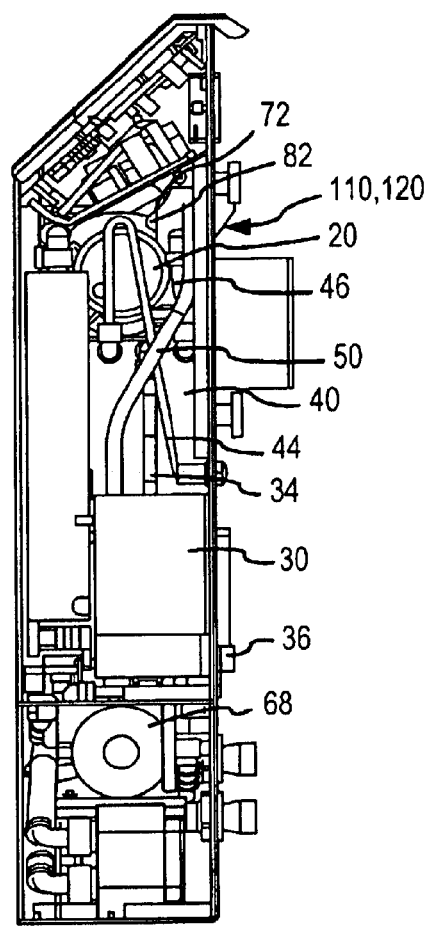

Of note, FIG. 2 illustrates the interconnection of one or more external patient temperature sensors 210 with the signal conditioning interface 140. Patient temperature sensor(s) 210 may comprise, for example, one or more bodily core temperature sensors (e.g. nasopharynegeal, esophageal, bladder, tympanic and rectal probes) that provide analog signals to the signal conditioning interface 140. In turn, the interface 140 provides digital signals to processor 130 for use in the application of preset temperature control algorithms. By way of primary example, the temperature data received from external sensor(s) 210 may be utilized at processor 130 to determine the amount and rate of thermal exchange to be affected by the system 10 in relation to preset/user-defined patient "target" temperatures. In turn, processor 130 may provide the appropriate control drive signals to heater 62, radiator/fan 64 and/or auxiliary pump 68. In addition to the components, FIG. 2 also illustrates that an external operating room data logger 220 and/or an external diagnostic processor 230 may be selectively interconnected via a data bus 174 to the processor 130. As will be appreciated, the ability to interface system 10 with logger 220 and/or processor 230 allows for the downloading and uploading of digital information, including information collected from one or more of the sensors of system 10 or digital information utilized in the processing of and response to the sensor information.

Figure 4:
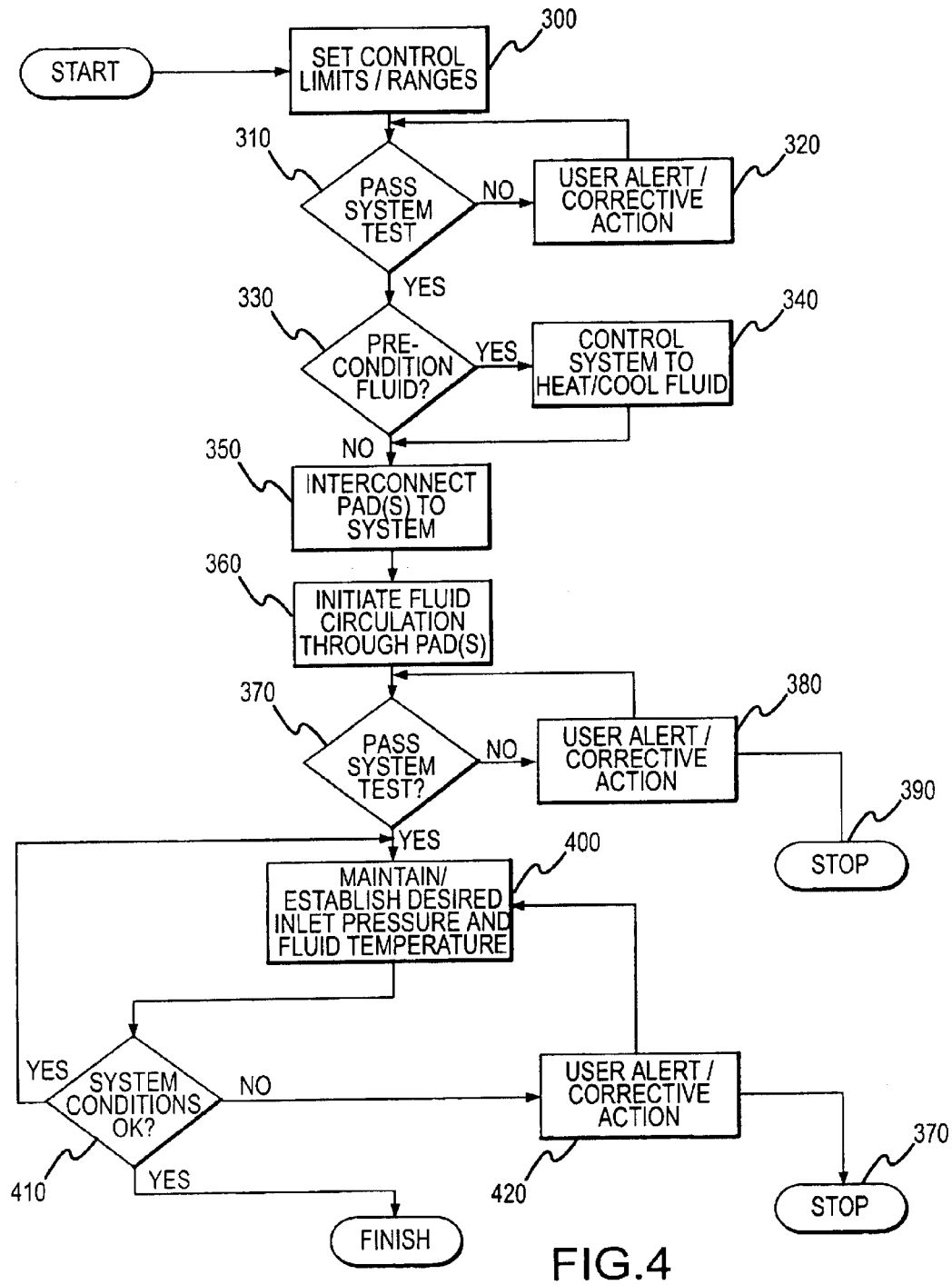
FIG. 4 is a process flow diagram of one embodiment of a patient temperature control method comprising the present invention.

Reference is now made to FIG. 4, which illustrates a process flow diagram of one embodiment of a patient temperature control method. Such method may be implemented in conjunction with operation of the system embodiment of FIGS. 1–3 and will be described in relation thereto to facilitate a better understanding of the various steps. It should be appreciated, however, that the methodology described here in below may be implemented in a variety of different system embodiments.

As shown in FIG. 4, the operation of system 10 may initially provide for the selective establishment of system control limits/ranges by a user (step 300). The setting of limits/ranges may be achieved by a user at input device 154 (e.g. via user-friendly prompting at displays 152). By way of example, the settable limits/ranges may include a targeted patient temperature, maximum/minimum patient temperatures, a target temperature for the circulated fluid, and maximum/minimum fluid temperatures.

Next, a system test may be completed (step 310) to confirm/calibrate key operational capabilities of the system 10. By way of example, such test may be automatically initiated upon completion of step 300 and/or otherwise may be selectively initiated pursuant to prompting at displays 152 and user input at input device 154. The system test may include any number of automated procedures initiated by processor 130 to confirm the operability of the various sensors, fluid handling devices, heat exchange devices and associated circuitry of system 10.

In particular, processor 130 may automatically transmit a test signal to temperature simulator 180 (e.g. comprising one or more resistors of known value(s)), thereby causing temperature simulator 180 to provide an analog signal input to comparator 166 for test purposes. For example, the test signal provided by processor 130 may cause temperature simulator 180 to provide an analog signal input to comparator 166 that exceeds a predetermined value (e.g. corresponding with a maximum temperature). Such signal should cause comparator 166 to transmit a signal to open switch 162 as well as a response signal to processor 130. In turn, processor 130 may monitor the response of switch 162 to confirm the operability of both comparator 166 and switch 162. The system test procedure may also include the provision of test signals from processor 130 to calibration simulator 182 (e.g. comprising one or more resistors). In turn, calibration simulator 182 may provide analog signals that are conditioned then employed by processor 130 to automatically calibrate the system 10 so that signals received from external sensors 210 during operation may be translated into accurate patient temperatures for display.

As illustrated in FIG. 4, if any of the system test procedures indicate a problem with system 10 (step 320), a user alert may be provided at user interface 150 (step 320). By way of example, visual alarms may be provided at displays 152. Additionally, and/or alternatively audible alarm signals may be provided at user interface 150. Upon the provision of the alarm output, a user may take appropriate corrective action to address the alarm condition. In this regard, the user interface 150 may display remedial instructions to a user and allow for user override in certain instances.

The process embodiment of FIG. 4 also provides for the optional preconditioning of fluid by system 10 (step 330). As previously noted, such preconditioning may entail the heating or cooling of fluid within system 10 prior to interconnection with one or more contact pad(s) 1. When time permits, such preconditioning may be desirable from the standpoints of both patient comfort and rapid patient temperature alteration. By way of example, the preconditioning step may be selectively initiated by a user via the input device 154.

Pursuant to the initialization of fluid preconditioning (step 330), various components of system 10 may be automatically and/or manually controlled (step 340). More particularly, and referring now to FIG. 5, bypass valve 92 of system 10 may be opened (step 500) via transmission of a control signal by processor 130. In turn, circulating pump 20 may be operated at a predetermined speed (step 510) pursuant to the transmission of control signals by processor 130. The opening of bypass valve 92 and operation of circulating pump 20 causes fluid within make-up reservoir 40 to flow through the bypass fluid line 54, through circulating pump 20, and back into the make-up reservoir 40 via circulating reservoir 30.

Figure 5:
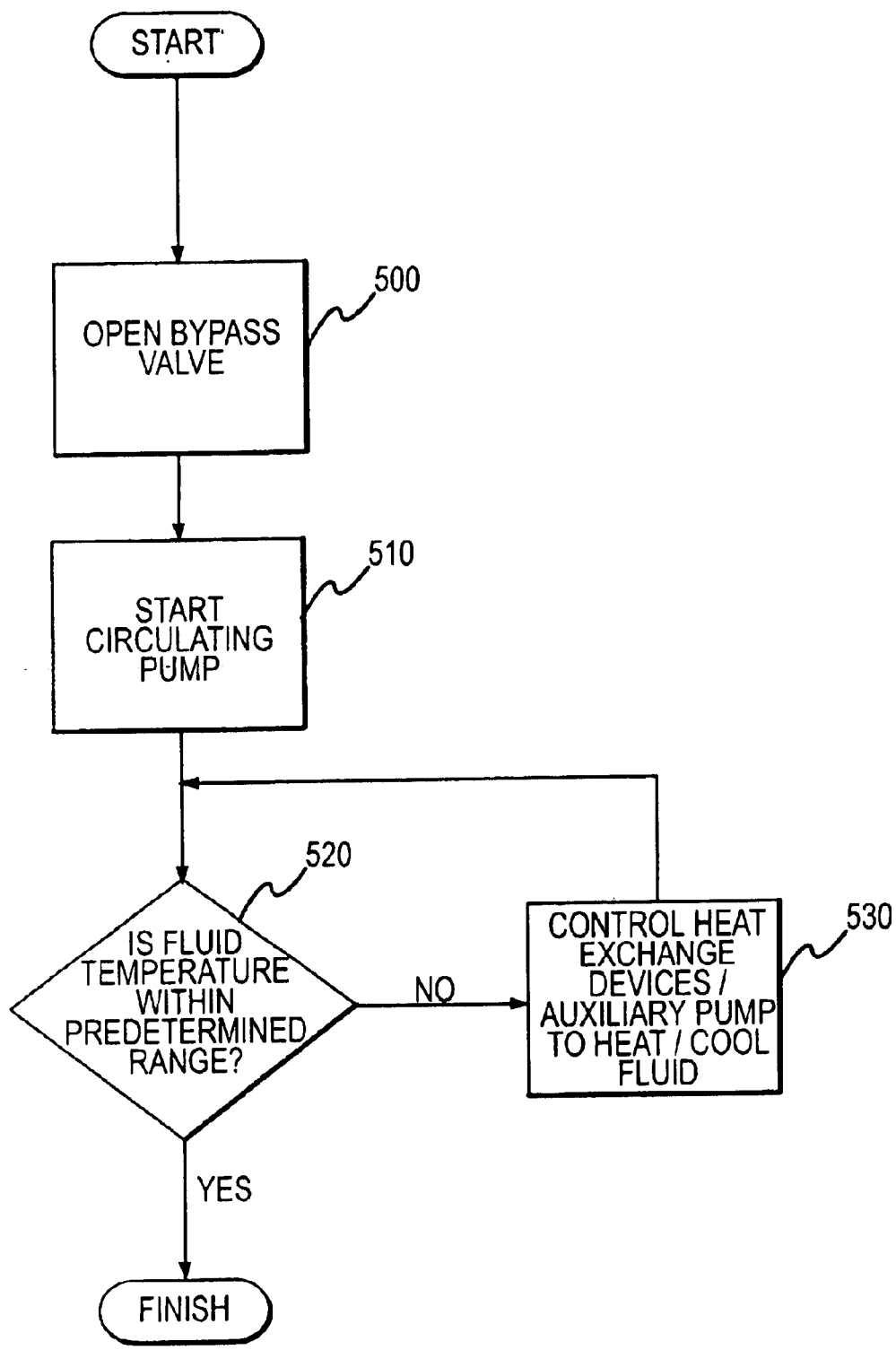
FIG. 5 is a process flow diagram for fluid preconditioning in the method embodiment of FIG. 4.

As indicated by FIG. 5, the fluid temperature may be sensed to determine if it is within a predetermined desired range (step 520). More particularly, temperature sensor 70 may be employed to sense the temperature of the fluid in circulating reservoir 30, wherein the sensed temperature signal is provided to processor 130 for comparison to a predetermined range. In the later regard, the predetermined range may be preset or otherwise established by a user in conjunction with set-up operations. In the event that the sensed temperature is not within the predetermined range, processor 130 may transmit control signals to heat exchange devices 62 or 64, and/or to auxiliary pump 68, to achieve the desired degree of fluid heating/cooling (step 530). As may be appreciated, the temperature sensing by sensor 70 and control of heat exchange devices 62, 64 and pump 68, by processor 130 may continue as needed to establish the desired fluid temperature.

Figure 6:
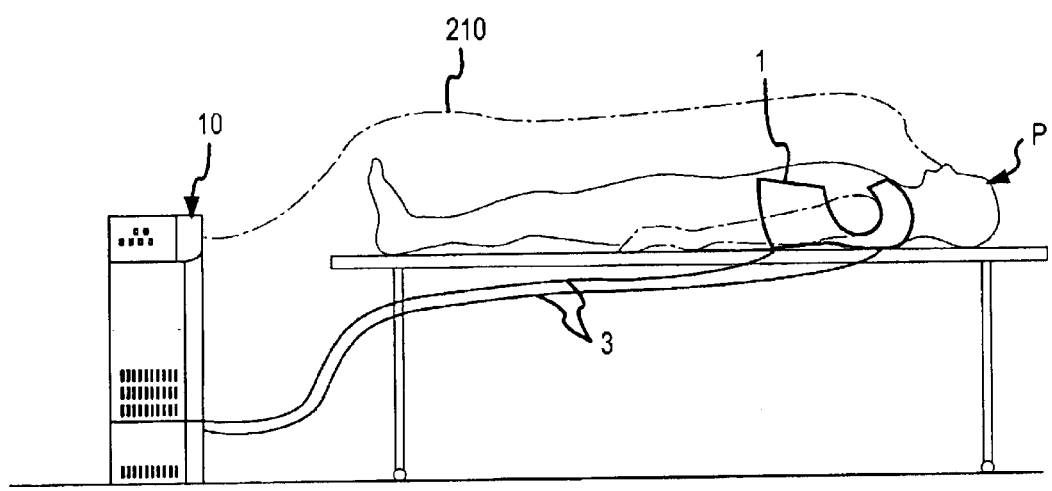
FIG. 6 is a diagrammatic view of an exemplary use of the present invention.
Figure 7:
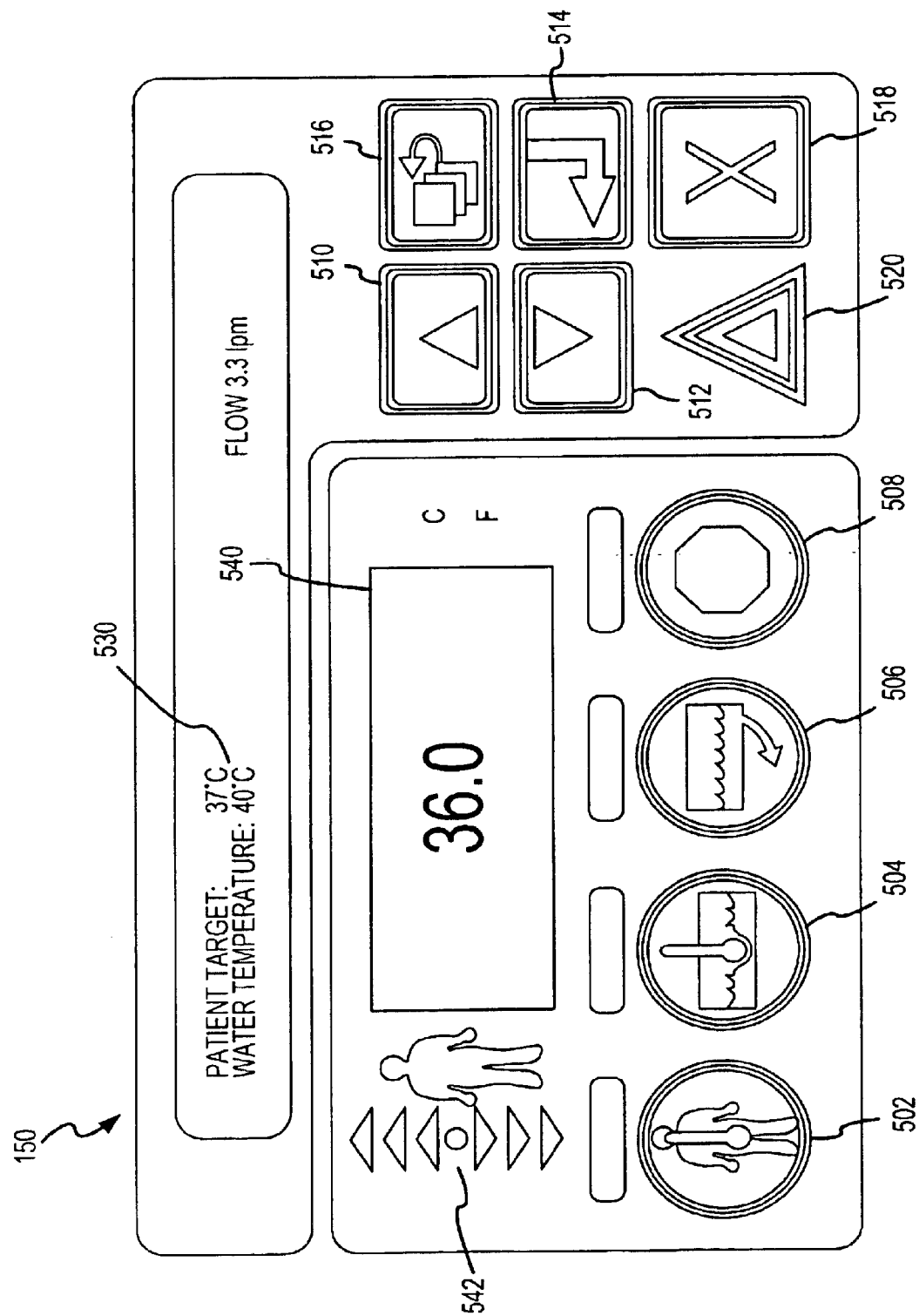
FIG. 7 is a front view of one embodiment of a user interface employable in conjunction with the present invention.
Figure 8A:
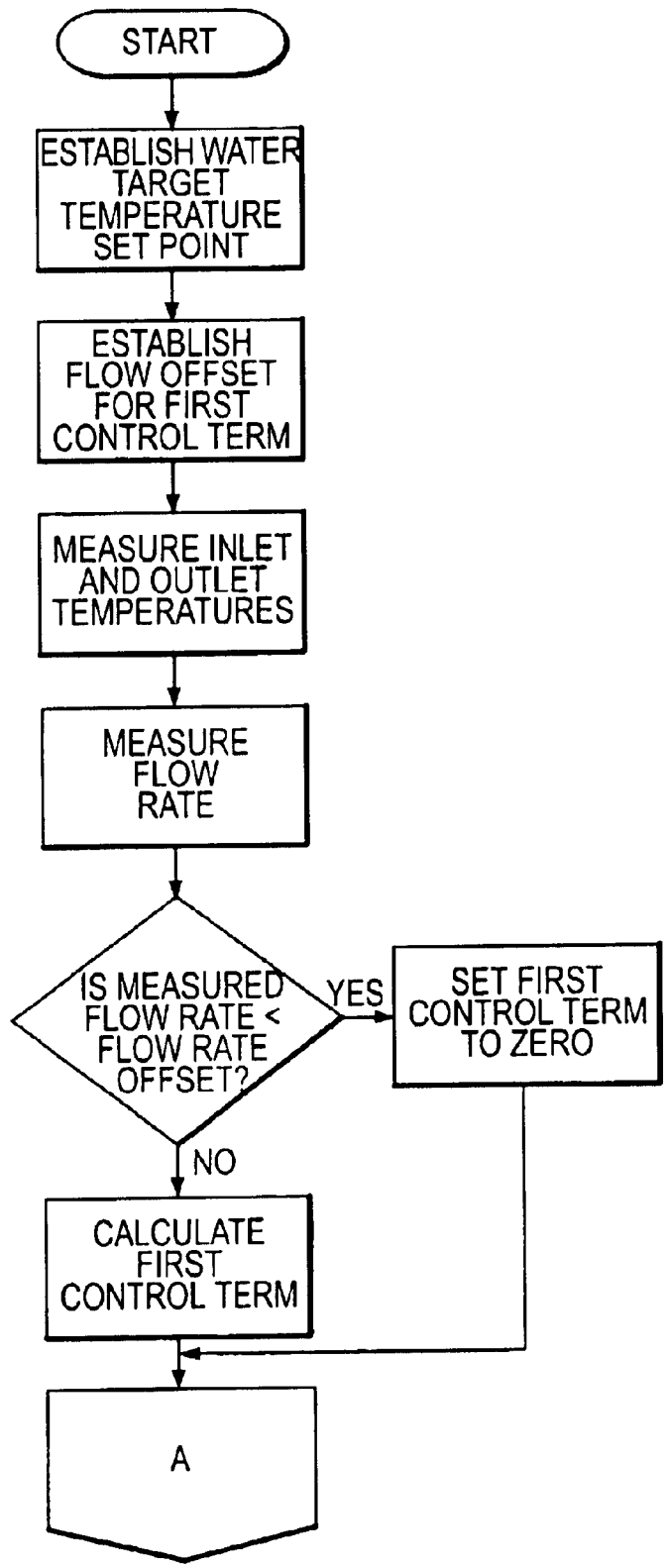
FIGS. 8a–d and b is a process flow chart describing the patient temperature control functions.
Figure 8B:
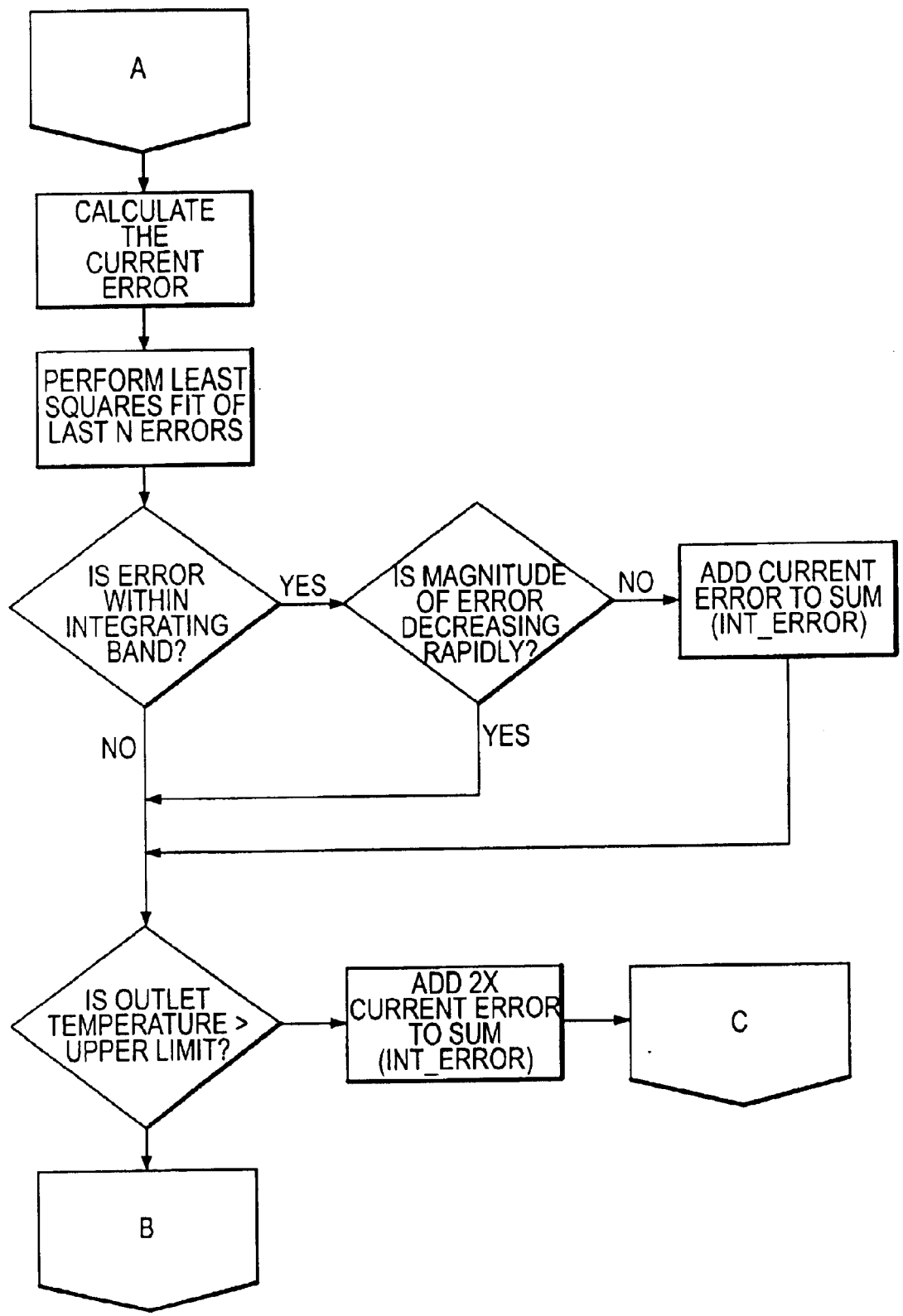
Figure 8C:
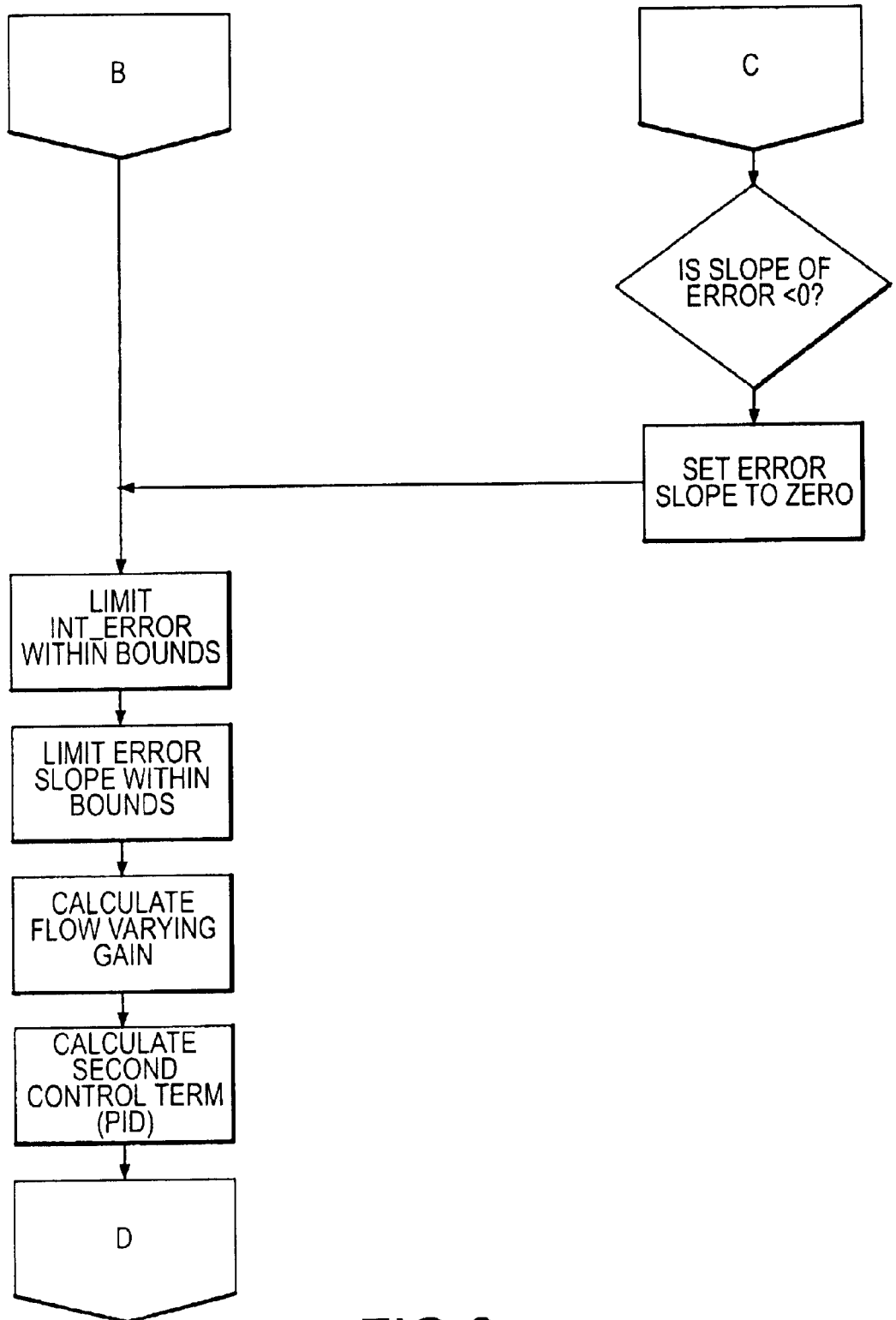
Figure 8D:
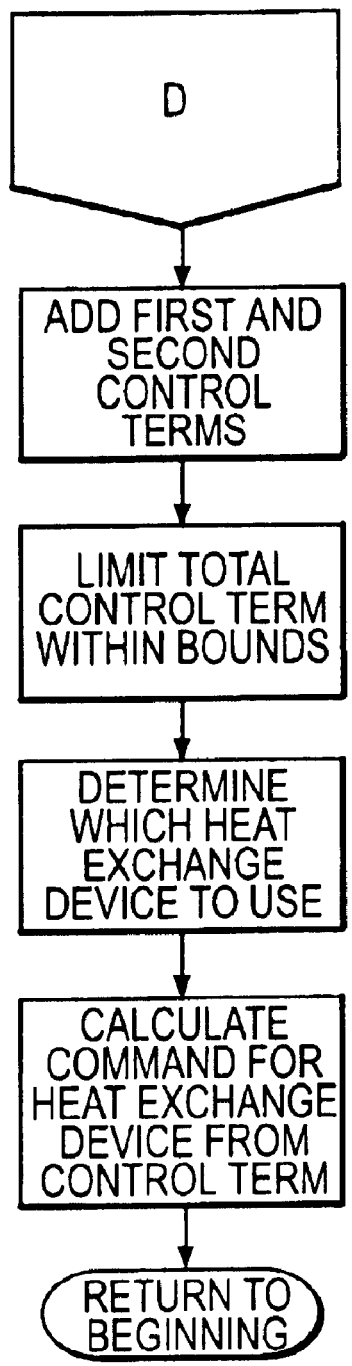

Returning now to FIG. 4, the initialization of actual patient heating/cooling entails the interconnection of one or more contact pads(s) 1 to the system 10 (step 350). In conjunction with such interconnection, system 10 may require a user to provide an appropriate control input at input device 154. After interconnection of the contact pad(s) 1, fluid circulation therethrough may be initiated (step 360). In this regard, appropriate user input may be required at input device 154, whereupon circulating pump 20 may be operated in accordance with a preset speed-setting algorithm. In conjunction with steps 350 and 360 noted above, the pad(s) 1 and patient should preferably be located above the system 10, as shown in FIG. 6.

At this point, further system testing may be provided (step 370). By way of primary example, processor 130 may utilize the signals provided by a flow meter 94 and/or pressure sensor 82, and the known operating speed of circulating pump 20, to determine if fluid is properly circulating through the system 10 and the interconnected pad(s) 1. More particularly, for a given operating speed of circulating pump 20 the pressure sensed by sensor 82 and the fluid flow measured by flow meter 94 should be predictable within a predetermined range under normal operating conditions. In the event that the signal received from flow meter 94 indicates a flow volume outside of the predetermined range, processor 130 may be provided to identify a condition of potential concern to a user as well as potential remedial action to be taken at user interface 150 (step 380). By way of example, a message may be provided at a display 152 to check for kinks in the tubing line 3 employed to interconnect pads 1 to the system 10. Further, processor 130 may be provided so that if system conditions fall outside of a predetermined range and/or are not corrected within a predetermined time, operation of circulating pump 20, heat exchange devices 62, 64 and/or auxiliary pump 68 is automatically terminated (step 190).

Assuming system 10 is operating within normal expected ranges, system 10 may be automatically controlled to provide the desired patient heating/cooling at interconnected pad(s) 1. In this regard, the inlet pressure at inlet port 120 may be maintained in a predetermined operating range and the temperature of the circulated fluid may be established to affect the desire heating/cooling of a patient through pads 1 (step 400). For purposes of maintaining the desired negative pressure in the interconnected pad(s) 1, processor 130 may utilize the sensed pressure signal provided by inlet pressure sensor 82 to control the speed of operating pump 20. For purposes of establishing the temperature of the circulating fluid the processor 130 may utilize one or both of the output signals from temperature sensors 72, 70 of system 10, as well as the sensed temperature signals provided by external temperature sensor(s) 210. Of note, it may be particularly advantageous to utilize all of such sensed temperature signals. More particularly, the utilization of all there signals allows for the computation of thermal exchange with a patient. In turn, control of the heat exchange devices may be set. In one arrangement, such setting may be provided utilizing the algorithm provided below:

$$W=KQ(T_i-T_t)-MCdT_{avg}/dt;$$

Where:
- W=Transfer of heat exchange devices 62, 64 and 66;
- K=Conversion of calories/minute to watts;
- Q=Water flow rate (e.g. measured by flow meter 94);
- $T_i$=Water inlet temperature (e.g. measured by sensor 72);
- $T_t$=Water target temperature (e.g. as set by a user);
- M=Mass of circulating water (e.g. as input to or determined by system 10);
- C=Heat capacity of water; and,
- $dT_{avg}/dt$=Rate of change of average circulating water temperature (e.g. as determined using measurements by sensor 70).

Returning now to FIG. 4, the output signals from sensors 70, 72, 74, 82 and 94 may be employed on a periodic basis to insure system operation within preset acceptable ranges (step 410). In the event monitored operations are outside acceptable limits user alerts for corrective action may be provided (step 420), and if the condition of concern continues operations may be automatically terminated (step 390).

With regard to the heat exchange algorithm described above, the system described herein may be further configured to employ additional algorithms which control the manner in which the system approaches and maintains a particular patient temperature set point. Referring again to FIG. 2, the processor 130 may access and employ one or more of these water temperature control algorithms during operation so that the water temperature may be affected in a controlled manner.

According to the invention described herein the water temperature control algorithm to be employed determines the power (energy per unit time) to be applied to the circulating water such that the water temperature rapidly approaches and then remains close to the desired set point temperature. The temperature control algorithms employed herein are further configured to reduce significant temperature oscillations around a selected patient temperature set point and include the capability to change water temperature in a rapid manner when one or more of the monitored temperature of the system are outside a preset range.

According to one embodiment of the invention, the applied power may be calculated using a combination of at least two control terms, where the first term is based on the water temperature measured at the inlet of the system, and the second term is based on the water temperature at the outlet. As part of this temperature control process, the outlet water temperature is the temperature that is driven to the set point. The first control term may be proportional to a calculated difference between the inlet water temperature and a patient temperature setpoint. More particularly the first control term may be the product of a gain, the measured flow rate with an offset term subtracted from it, and the difference between the water temperature set-point and the measured inlet water temperature. This may be calculated with the following equation:

Control Term 1=Gain×(Measured Flow Rate−Flow Offset)× (Water Temperature Set-Point−Measured Inlet temperature)

According to the above equation, if the measured flow rate is less than the flow offset, control term 1 is set to zero.

If the flow offset term is set to zero, the gain can be chosen so that control term 1 is equal to the heat transfer rate require to raise or lower the circulating water from the measured inlet temperature to the water temperature set point. Although control term 1 will provide a theoretical temperature change for changing the water temperature to the temperature set point, the algorithm may be further refined to take into account real world characteristics of the system described herein.

One characteristic in particular may be that in reality the actual heat input rate or applied power will not exactly match the commanded value. This is especially true in the situation where more than one heat exchange devices are employed to provide heat transfer. In essence, the heater can only apply heat and the radiator, refrigeration device, ice or some other device, may only be employed to cool. Further, the actual power applied by the heater can vary from the command value due to variations in line voltage, heater electrical resistance, and losses of heat to the environment. The power removed by the cooling device can be influenced by the ambient air temperature, partial blocking of airflow and a variety of other factors.

A second characteristic which may be taken into account is that the application or removal of heat from the water is not instantaneous. The required heat transfer rate determined at one instant in time cannot be applied at that instant. More specifically, even in the fastest system some delay will occur between the point in time which the command is initiated and the amount of time the heat exchange device takes to either cool down or heat up to a specified level, and then the amount of time it takes to add/remove the heat from the water.

A third characteristic which may be taken to account are the limits to the amount of heat that can be added or removed for a particular amount of water. For example, a radiator cannot be operated below a certain flow rate, such that certain minimum temperatures will not be reachable.

To take into account the characteristics described above, the gain may be set to a lower value than that which will result in the theoretical required heat transfer rate, and a non zero flow offset term may also be included. The flow offset term reduces the value of control term 1 at low flow rate to reduce the impact of the heat transfer delay described above.

The second control term is mainly focused on controlling the rate of change of water temperature as well as the damping of oscillation around the temperature set point. The second term is calculated using the difference between the water temperature set-point and the measured outlet temperature. As was described above, the measured outlet temperature is measured at the outlet of the system before the water circulates through the temperature control pads. The algorithm for calculating the second term, according to the invention described herein, may be based on a proportional, integral, and derivative (PID) controller with several modifications.

A PID controller employable herein may be represented by the following equation:

$$\text{PID Control} = K_p \times \text{Error} + K_I \times \text{Integral (Error)} + K_d \times \text{Derivative (Error)}$$

Where:

$K_p$=Proportional gain $K_I$=Integral Gain $K_d$=Derivative gain

Error=Measured temperature between the outlet temperature and the set point.

The equation used by the water temperature control algorithm to calculate the second term is:

$$\text{Control Term 2} = \text{Variable Gain} \times (K_p \times \text{Error} + K_I \times (\text{Modified Integral (Error)})) + K_d \times (\text{Modified Derivative (Error)})$$

The variable gain is calculated using the measured flow rate of the water through the system. As was described above, flow rate is calculated using a flow meter. Variable gain is calculated by the following equation:

$$\text{Variable Gain} = K_0 + K_1 \times \text{Measured Flow Rate}$$

Although this is just one representation of an equation to calculate gain, one skilled in the art will realize that other variations may be employed.

In reviewing the above equations, it is seen that the variable gain increases as the measured flow rate increases. As would be understood through further study of the system, the rate of heat transfer required to raise the water temperature by a given amount must increase as the flow rate increases. Also, since the outlet water temperature is measured downstream of the heater and cooling device, there is a time delay between the application of heat to, and the measurement of the temperature of a given bolus of water. This time delay increases as the flow rate decreases.

As is understood in the analysis of control systems, time delays tend to cause oscillation and overshoot in a control system. As the time delayed increases the response of the control system must be slowed to reduce the overshoot. This can be achieved by reducing proportional and integral gain, $K_p$ and $K_I$, and by increasing the derivative gain $K_d$. With measurement noise, a large derivative can cause the control system to become unstable. As such, the variable gain is used to reduce the proportional gain and integral portions of the control term while leaving the derivative unaltered. As a result, the derivative term contributes a larger portion of the control term at lower flow rates.

The water flow rate through the system described herein is related to the number of temperature control pads connected to the system. The number of pads is directly related to the heat transfer surface area, which is related to the heat transfer load on the machine. As the flow rate increases, the heat load generally increases. The control system described herein is configured such that it becomes more responsive as the load increases.

The integral term described herein is configured so as to eliminate steady state error. According to the system described herein, if there is a small, slowly changing error, the integral of the error gradually increases over time to drive the error to zero. However, the presence of a time delay in the system, combined with an integral feedback can result in overshoot and oscillation.

In order to avoid temperature extremes which may affect system operation, it is important to keep the temperature overshoot to a minimum. The modified integral term described above is adapted to reduce the overshoot and oscillation by limiting the conditions under which integration is allowed. In a sampled data system, the integral is approximated by a summation of errors over time. According to the control system described herein, the current error is added to the modified integral term only if the magnitude of the error is decreasing very slowly or increasing at any rate. Integration may be further restricted so that the integral is not changed if the magnitude of the error is larger than a prescribed value (e.g., 0.5° C.). The maximum and minimum value of the modified integral term are also limited so that it does not become too large a portion of the overall control.

The derivative is usually approximated by the difference between two consecutive measurements divided by the sampling time internal. In a system with measurement noise, this can result in large variations in the approximated derivative which can cause large variations in the control term. This may be addressed with digital filtering, however, the signal to noise ratio may be so large that the filtered result is not a good approximation.

The modified derivative term employed herein may be calculated by determining the slope of a "running least squares" line fit to the most recent N data points. The derivation of this approximation may be performed as follows:

To determine the derivative, fit a line through the most recent N data points. Given the points $(T_i, T_1)$ the least squares line fit through the points, $$T = A + Bt$$

Is determined from:

$$A = \frac{(\sum t_i^2)(\sum T_i) - (\sum t_i)(\sum t_i T_i)}{N N(\sum t_i^2) - (\sum t_i)^2}$$

$$B = \frac{N \sum t_i T_i - (\sum t_i)(\sum T_i)}{N(\sum t_i^2) - (\sum t_i)^2}$$

The estimate of the derivative is the slope B. To keep a running least square slope estimate:

$$\text{Sum Temperature} = \sum_{i=h-n}^{h} T_i$$

$$\text{SumTime} = \sum_{i=h-n}^{h} t_i$$

$$\text{Sum Time Temperature} = \sum_{i=h-N}^{h} t_i T_i$$

If it is assumed that the first data point in the series falls on the line:

$$T_{h-n} A = B t_{h-n}$$

In estimating the slope, use a "sliding" T axis and set $$T_{h-N} \cong A$$

With these assumptions, $\sum_{i=h-N}^{h} t_i = \tau \sum_{i=o}^{h} i = 0 + 1 + 2 \ldots N - 1 = \text{Const}$ $$\sum_{i=h-N}^{h} t_i T_i = T(0 * T_{h-N} + 1 * T_{h-n+1} + 2 * T_{h-N+2} + \ldots (N-1) T_h)$$

$$\sum t_i^2 = \text{Const} \left( \sum t_i \right)^2 = \text{Const}$$

$$\sum_{i=h-N}^{h} t_i T_i \bigg|_{new} = \sum_{i=h-N}^{h} t_i T_i \bigg|_{old} - \tau \sum_{i=h-N}^{h} T_i \bigg|_{old} + (N-1)\tau T_h \bigg|_{new}$$

$$\sum_{i=h-N}^{h} T_i = \sum_{i=h-N-1}^{h-1} T_i - T_{h-N-1} + T_h$$

Assume $T_{h-N-1} = A_{old}$, then $$\sum_{i=h-N}^{h} T_i = \sum_{i=h-N-1}^{h-1} T_i - A_{old} + T_h$$

Because the set point is filtered, the temperature error is used in the above calculations instead of the temperature so that the controller responds appropriately to changes in set-point.

With regards to the least squares slope calculation the following example constants may be employed:

```
Sum time = 45;        \*(0+1+2 . . . 9) not sum time
Sum time squared = 285;   *(1+4+9+ . . . +8)
Delta = 825;  \*10^-num-samples*sum time square - (sum - time)2
Tau = 1;      \*sampling period
Num Samples = 10   \*number of samples being used
The variable may include:
Sum time error       \*sum of time temperature error
Sum error            \*sum of errors
Error intercept      \*least squares intercept term
Error slope          \*least squares slope
Initially all variables are set to zero
Sum time error = sum time error = τ * sum error +
                Num sample * τ * error + error intercept
Sum error = sum error - error intercept + error;
Error intercept = (sum time square * sum error -
                sum time * sum time error) / Delta;
Error slope = (num samples * sum time error - sum time * sum error)
                /Delta;
```

The magnitude of the modified derivative term may also limited to prevent response to noise.

In employing the above-described processes, various safety features may also be incorporated into the system. More specifically, one or more alternative processing modes may be employed if certain monitored conditions are detected. For example, if the water temperature is either too high or too low, an alternative mode of operation may bring the water temperature into a safe zone as quickly as possible. Prior to operation, a maximum allowed water temperature set-point may be set (e.g. 42° C.). Temperatures above this value may be dangerous to a patient. The algorithm described herein may be configured such that it responds differently above 42° C. to quickly drop the water temperature back to a safer level. In order to perform in this mode, the modified integral term may be incremented at a faster rate. This may be done by multiplying the modified integral term by a weighting factor. Further, the derivative term is disabled (set to zero) while the temperature is dropping. A non-zero derivative term will may be tend to slow the rate of temperature drop. Conversely, in the situations where the system described herein is employed to induce hypothermia, if the temperature drops below a designated minimum, the modified integral and derivative terms may be further modified in order to provide for a rapid increase in temperature.

A typical operational mode for the system described herein is disclosed in the flow charts of FIGS. 8a–d. Depending on particular mode of operation for the temperature control system, a temperature set-point for the water will be selected by a system user prior to preparation or identified as part of a preprogrammed sequence. For example, in the situation where the temperature control pads are to induce hypothermia, the temperature set-point will be selected to cool accordingly. Conversely, if the temperature control system is in a warm up mode, the temperature set-point is selected to provide the desired amount of body heating. Also at this time, a flow off set value is established. During operation of the system, the water temperatures at both the inlets and outlets of the system are measured on a periodic basis.

As an initial step in calculating a power signal, a first determination may be made as to whether the current measured flow rate is greater than the selected flow offset. If the measured flow rate is less than the flow offset, the first control term is set to zero and the calculation process continues. If the measured flow rate is not less than the flow offset, the first control term is calculated using the equation with readings from the various sensors from above.

With the first control term calculated for the particular time period, the process continues to calculate the second control term. At this point a measurement is made of the outlet temperature. The current error value is then calculated which is the difference between the measured outlet temperature and the set-point temperature.

The current error is then combined with previous data to calculate a rate of change. The last N errors are identified and a "running least squares" line fit, as was described above, is calculated. This rate of change is used to identify the modified derivative. If there are less than N errors available, only those points available are employed to make the calculation.

The value of the current error is then compared to a pre-determined error range, the integrating band. If the error value is not within the integrating band, the error value is not added to the summation used as an estimate of the integral of the error over time. This effectively turns the integral portion of the control term off until the measured temperature is close to the set point temperature. This helps to reduce overshoot and oscillation. The integral term is intended to reduce or eliminate steady state error. When the error is large, it is being driven rapidly towards the set point and is not at steady state. Adding the error to the integral sum only when the error is small prevents the integral portion of the controller from responding to non steady state errors.

If the error is within the integrating band, a determination is then made as to whether the magnitude of the error is decreasing rapidly. If the magnitude of the error is not decreasing at or above a pre-determined rate, it is added to the integral sum. Otherwise the integral sum is unchanged. Since, by definition, a steady state error does not change, using the rate of change of error to determine whether to add to the integral sum ensures that the integral term only responds to steady state errors. This prevents the integral term from over compensating which could cause overshoot and oscillations.

Once the steps for calculating the integral sum are complete, a further determination may be made as to whether the outlet temperature exceeds an upper limit. As was described previously, in situations where the measured temperature exceeds a maximum temperature or falls below a minimum temperature the system will initiate a mode of operation which may be configured for a rapid drop or rise, respectively, in temperature. In this situation, a weighting factor may be added to the current measured error (in this case the error is multiplied by two) and this modified error is added to the integral sum.

A further query may be made as to whether the slope calculated for the least squares fit of the accumulated errors is negative. If it is negative, it indicates that the temperature is decreasing, and as such, the slope may be set to zero which effectively disables the derivative term and increases the rate of temperature change.

At this point, the modified integral and derivative terms have been calculated and both terms may be limited so as to not be outside a pre-determined range. These ranges are established so that the modified integral term does not become too large a portion of the overall control term. The final component of the second control term to be calculated is the flow varying gain. As was mentioned above, this may be done using signals received from the flow meter.

With the variable gain and the modified derivative and integral terms calculated, control term 2 may be calculated and then added to control term 1 in order to generate a total control term. The total control term may also be limited within a predetermined range. Finally, a determination may be then made as to which heat exchange should be employed, and based on the selected device a command signal is then generated and transmitted. This above described control process is then repeated on periodic basis depending on the system programming and/or the manual operation by a system user.

Reference is now made to FIG. 6, which illustrates one embodiment of a user interface 150. Such interface 150 will be described to in relation to an exemplary application of various features of the system 10 described above. The user interface 150 comprises user operating keys 502–518, a message screen 530, and a patient temperature display 540. The message screen 530 displays parameter settings, warnings, and alarms during operation.

If a patient temperature sensor 210 is utilized in a given procedure, display 540 provides the measured patient temperature. In one arrangement, display temperatures should range from 25° C. to 42° C. With a patient temperature sensor 210 in place, icon 542 indicates trends or changes in patient temperature. As shown, icon 542 may comprise a plurality of upward oriented and downward oriented arrows with a circle disposed therebetween. An illuminated upward yellow arrow indicates that a patient's temperature is rising. An illuminated downward yellow arrow indicates that a patient's temperature is falling. The higher or the lower the illuminated arrow, the faster the temperature is changing. When only the yellow circle is lit, the temperature of the patient is substantially constant.

Four main modes of automated operation of system 10 can be set utilizing keys 502–508:

1. "Patient Temperature Control Mode"—set by pushing key 502;
2. "Water Temperature Control Mode"—set by pushing key 504;
3. "Purge Mode"—set by pushing key 506; and,
4. "Stop Mode"—set by pushing key 508.

Additional information about a particular mode and modification of corresponding parameter settings may be achieved by pressing the "Up Arrow" key 510 or "Down Arrow" key 512 while in the given mode, as will be further described.

In the Patient Temperature Control Mode system 10 automatically functions to monitor and control a patient's temperature to a set target temperature. Water will be cooled or warmed as needed and pumped through the pad(s) 1 to achieve the target temperature. In one arrangement, patient temperature can be controlled and monitored between 33° C. and 37° C. When activated, a yellow indicator light over the key 502 is illuminated. A water flow rate will be displayed on the message screen 530 in liters per minute (i.e. "lpm"). In the Water Temperature Control Mode system 10 automatically functions to flow temperature-controlled water through the pad(s) 1. Water is controlled to a specific target temperature set by the operator. In one arrangement, the target water temperature and can be set between 4° C. and 42° C. When activated, a yellow indicator light over key 504 is illuminated. Unless an alarm condition occurs, water temperature and flow rate will be displayed in the message screen 530 when this mode is active.

In the Purge Mode system 10 automatically functions to empty water from the pad(s) 1. When the mode is activated a yellow light over key 506 is illuminated. A message (e.g. "Purging Water") will be displayed on the message display screen 530 when this mode is active. When pad(s) 1 have been emptied, the system 10 may be provided to automatically return to Stop Mode.

Pressing the Stop Mode key 508 at any time will stop any of the three other modes (i.e. Patient Temperature Control, Water Temperature Control Mode, or Purge Modes). When activated, the yellow light over the Stop Mode key 508 is illuminated. Any other mode can be activated from Stop Mode by pressing the corresponding mode key.

A variety of system settings and other information may be accessed from menus and information listings displayed at message screen 530 in the Stop Mode, Water Temperature Control Mode, and Patient Treatment Mode, including e.g.:

1. Set patient target temperature;
2. Set water target temperature;
3. Measured water level;
4. Set maximum/minimum water temperatures;
5. Set high and low patient temperature warning settings; and,
6. Other setup parameters (e.g. data output intervals).

As may be appreciated, the noted settings may be changed for each procedure. The system 10 may be provided so that once the system 10 has been turned off, settings return to default parameters. New default parameters can also be permanently saved if desired.

As noted above, the "Up Arrow" key 510 and "Down Arrow" key 512 allow users to scroll through menus and information listings on the message screen 530. Relatedly, the "Enter Key" 514 allows an operator to select and change parameter settings. For example, a given parameter listed on message screen 530 may be selected using arrow keys 510, 512, then the Enter key 514 may be pressed, causing the parameter to be displayed in a pronounced manner (e.g. brightened or varied color illumination). Next, the arrow keys 510, 512 may be utilized to increase or decrease the setting value. When the desired value is displayed, the user may then press the Enter key 514 again to establish the setting. The "Return to Main Menu Key" 516 will exit a given menu and return a user back to a main menu. The "Alarm/Alert" icon 520 is automatically illuminated upon detection of an alert or alarm condition. Pressing the "Cancel Key" 520 clears an alert or alarm.

Prior to use of the system 10, the reservoirs 30 and 40 should be filled with fluid, e.g. distilled or sterile water. To do so, the system 10 should be connected to a power source 160, e.g. via plug-in to an appropriate power supply outlet. After being turned on, the system 10 may be provided to conduct a brief self-check and enter the Stop Mode. The yellow light over the Stop Mode key 508 will be illuminated. Using the "Down Arrow" key 512, a user may scroll through the menu until the display reads "WATER LEVEL "XX" Uses—Press Enter to Fill". A user may then connect a fill tube into one of the inlet connectors on the block manifold 5. The other end of the fill tube may be placed into a water container. The Enter key 514 may then be pressed to cause system 10 to start filling and automatically stop when it is complete. The system 10 will then return the Stop Mode.

The filling process can be interrupted at any time by pressing the Stop Mode key 508; however, the reservoirs 30, 40 may not be adequately filled for the maximum number of uses. To determine how many procedures may be run before refilling (e.g. assuming a design limit of a predetermined number of pads), a user may use the Up and Down Arrow keys 510, 512, to scroll through the menus until the message screen 530 displays the water level and number of uses left. As noted, many parameters for controlling temperature with the system 10 may be changed and/or customized and saved for future use. Prior to using the system 10 for a given patient, a user may determine which settings will be used. All parameters will return to default setting unless new settings are saved.

Treatment parameters can be accessed while the Stop Mode key 508 is lit. A user may press the Up Arrow key 510 or Down Arrow key 512 to scroll through the various menu options.

In one arrangement, the default settings and ranges of options may be set as follows:

| Parameter | Default | Options |
|---|---|---|
| User Selected Operational Settings: | | |
| Data Output Interval | 1 minute | Off, 5 seconds to 10 minutes<br>Intervals from 5 to 60 seconds - 5 seconds<br>Intervals from 1 to 10 minutes - 1 minute |
| Data Output Format | Compacted | Compacted or Detailed |

| Parameter | Default | Range | Incremental Changes |
|---|---|---|---|
| User Selected Treatment Modes: | | | |
| Patient Target Temperature | 37° C. | 33.0° C. to 37.0° C. | 0.1° C. increments |
| Water Target Temperature | 37° C. | 4.0° C. to 42.0° C. | 1.0° C. increments |
| Maximum Water Temperature | 42° C. | 32.0° C. to 42.0° C. | 1.0° C. increments |
| Minimum Water Temperature | 4° C. | 4.0° C. to 32° C. | 1.0° C. increments |
| User Adjustable Alerts: | | | |
| Patient High Temperature Alert | 42.0° C. | 25.1° C. to 42.0° C. | 0.1° C. |
| Patient Low Temperature Alert | 25.0° C. | 25.0° C. to 41.9° C. | 0.1° C. |

| Parameter | Default | Incremental Changes |
|---|---|---|
| Chiller Connected for Cooling | No | Yes or No |

To change any of the default settings, from the Stop Mode a user may utilize the following procedure:

1. Use the Up Arrow key 510 and Down Arrow key 512 to access a setting that will be displayed on the message screen 530.
2. Press the Enter key 514 and the parameter that can be modified will be highlighted.
3. Press the Up Arrow key 510 or Down Arrow key 512 to reach the desired settings. Press the Enter key 514 to save.
4. To change additional settings, continue to scroll through the menu, pressing the Up Arrow key 510 or Down Arrow key 512 to access the appropriate screens.
5. Repeat the procedure to highlight, select, and save the displayed parameters.
6. The newly configured parameters will remain throughout a given procedure until the system 10 is turned off.

All customized parameters can be permanently saved or until a user decides to change them. To save the newly set parameters as defaults settings a user may utilize the following procedure:

1. Scroll through the menu screen until a "SETUP" screen is displayed.
2. Press the Enter key 514 and scroll through the menu until "Save Current Settings" is displayed.
3. Press the Enter key 514 to save the settings.

Then, a temperature sensor 210 may be placed in the patient and connected to the system 10. Thereafter, the patient's temperature can be monitored and controlled.

To continue patient treatment, a user may press the Stop Mode key 508 and confirm all of the parameters are programmed to the desired setting using menus provided when the Stop Mode key 508 is activated, as described above. The following settings are of primary note:

1. Patient target temperature: determines the temperature set-point for the patient. Temperature set range may be limited to 33° C. to 37° C.
2. Maximum water temperature: allows a user to determine the highest water temperature that will circulate through the pads during Patient Treatment Mode.
3. Patient temperature high limit or low limit alerts: allows a user to determine patient temperatures at which the system 10 should provide an alert.

Next, a user may press the Patient Temperature Control Mode key 502. Thereafter, the message screen 530 will show the set patient target temperature, the current water temperature and the current water flow rate in the system 10. For certain procedures or before a temperature sensor 210 is placed, a warming or cooling cycle can be initiated without controlling temperature. The Water Temperature Control Mode can be used to circulate temperature-controlled water without automatically controlling patient temperature. This mode may be used whether or not a temperature probe has been placed. To do so, a user may access a water target temperature screen by pressing the Up Arrow key 510 or Down Arrow key 512 while in either the Stop Mode or Water Temperature Control Mode. Then a user may adjust the water temperature to a desired setting as follows:

1. Press the Up Arrow key 510 or Down Arrow key 512 until the following appears in message screen 530: "Water Target Temperature 37° C., Enter to Change".
2. If a new water target temperature is desired, press the Enter key 514 to highlight the temperature.
3. Press the Up Arrow key 510 or Down Arrow key 512 until the desired temperature is displayed. Press the Enter key 514. Changes can be made in increments of 1.0° C./F. between 4.0° C. and 42° C.

Once the water target temperature is set, and mode key 502 is pressed, the system will begin to adjust the water temperature to the desired setting. Flow rate will be shown on the message screen 530. Flow rate may vary depending on the size of the patient, the style of the pads used, and the number of pads that are applied.

As noted, system 10 may incorporate features into the system 10 that allow a user to pre-program certain alarms, including:

1. Patient temperature alerts; and,
2. Water temperature alerts.

In particular, the system 10 may provide a default alarm that will warn when a patient temperature exceeds a set level, provided water temperature continues to rise or stays above that set level. There is also a default alarm that will warn a user when a patient temperature falls below a set level, provided water temperature continues to decrease or stays below that set level.

The high and low patient set temperature alerts can be established by a user as follows:

1. While in Stop Mode, scroll through the menu using the Up Arrow key 510 or Down Arrow key 512 until the screen displays, "Patient Temperature High Alert 42° C., Enter to Change" or "Patient Temperature Low Alert 25.0° C., Enter to Change".
2. Press the Enter key and select the new temperature by using the Up Arrow key 510 or Down Arrow key 512. The high temperature range may be provided for adjustment between 25.1° C. and 52.0° C. in 0.1° C. increments. The low temperature range may be provided for adjustment between 25.0° C. and 51.9° C. in 0.1° C. increments.
3. Press the Enter key to save. As may be appreciated, numerous additional alerts and alarms may be provided.

More generally in that regard, it should be noted that the foregoing description is strictly for the purpose of facilitating an understanding of the invention and is not otherwise intended to limit the scope thereof, as defined by the claims which follow.

What is claimed is:

1. A method of providing temperature control in a temperature control pad system, comprising the steps of:

monitoring water temperatures in a plurality of locations in the temperature control system wherein the locations include an inlet and an outlet of the system;

calculating a first control term corresponding to a heat transfer rate required to raise or lower the circulating fluid from the inlet temperature to a preset fluid temperature set-point; and calculating a second control term related to a second calculated difference between the detected outlet temperature and the selected set point; and generating and transmitting a power signal to at least one heat exchange device, where the power signal is proportional to a mathematical combination of the first and second control terms.

2. The method of claim 1 wherein the heat exchange device includes at least one of:

a water heating device and water cooling device.

3. The method of claim 2 wherein the first control term is calculated as follows:

first control term=Gain×(Measured Flow Rate−Flow Offset)× (Fluid Temperature Set Point−Measured Inlet Temperature).

4. The method of claim 2 wherein the second control term is calculated using a PID controller which further includes a modified integral term, a modified derivative term and a variable gain.

5. The method of claim 4 wherein the second control term is calculated with the following:

second control term=Variable Gain×($K_p$×Error+$K_i$×(Modified Integral (Error))+$K_d$×(Modified Derivative (Error))

where:

Variable gain=$K_0$+$K_1$×Measured Flow Rate.

6. The method of claim 5 wherein the modified integral term is configured to reduce overshoot and oscillation in the control system by using the rate of change of a measured temperature error to determine when to add the measured temperature error to an integral sum relating to the (Modified Integral (Error)).

7. The method of claim 6 wherein the modified derivative term is calculated using a least squares fit for N number of measured temperature errors.

8. The method of claim 6 further comprising the step of detecting at least one of the inlet and outlet temperatures outside a predetermined range and initiating a temporary mode of operation.

9. The method of claim 8 wherein the temporary mode of operation comprises:
- calculating first and second control terms and accelerating a change of the modified integral term by multiplying a measured temperature error by a weighting factor and adding it to the integral sum;
- setting the modified derivative term to zero when the outlet and/or inlet temperatures begin moving toward the predetermined range; and
- resuming normal operations when the outlet and/or inlet temperatures are within the predetermined ranges.

10. A temperature control system for use in patient temperature control comprising:
- a system controller electrically connectable to a plurality of temperature sensors and a flow meter, wherein signals received indicate inlet temperature of fluid circulating from at least one temperature control pad, outlet temperature for the fluid circulating to at least one temperature control pad, and flow rate for the circulating fluid; and
- said system controller further configured to identify a first control term proportional to a first difference in temperature between the inlet temperature and a selected set point, and a second control term proportional to a second difference between the outlet temperature and a selected set point, wherein the first and second control terms are further employed by the system controller to generate a power signal transmittable to at least one heat exchange device configured to affect the temperature of the circulating fluid.

11. The system of claim 10 wherein the controller is electrically connectable to an inlet temperature sensor, outlet temperature sensor, an inlet pressure sensor and a flow meter which provides a signal from which flow rate may be calculated.

12. The system of claim 10 wherein at least one heat exchange devices includes at least one of: a first heat exchange device configured for heating the circulating fluid and a second heat exchange device configured for cooling the circulating fluid.

13. The system of claim 10 wherein the first control term is modeled to be a theoretical heat transfer rate required to raise or lower the circulating water from the measured inlet temperature to the water temperature set-point.

14. The system of claim 13 wherein the first control term may be determined from: Gain×(Measured Flow Rate−Flow Offset)×(Fluid Temperature Set Point−Measured Inlet Temperature).

15. The system of claim 10 wherein the system controller is further configured to include a second control term which is calculated using a PID controller which further include a modified integral term, a modified derivative term and a variable gain.

16. The system of claim 15 wherein the second control term is calculable by the following:

$$\text{second control term} = \text{Variable Gain} \times (K_p \times \text{Error} + K_1 \times (\text{Modified Integral (Error)}) + K_d \times (\text{Modified Derivative (Error)}))$$

where:
Variable Gain=$K_0 + K_1 \times$Measured Flow Rate.

17. The system of claim 16 wherein the modified integral term is configured to reduce overshoot and oscillation in the control system by using a rate of change of a measured temperature error to determine when to add the measured temperature error to an integral sum relating to (Modified Integral (Error)).

18. The system of claim 17 wherein the modified derivative term is calculated using a least squares fit for N number of measured temperature errors.

19. The system of claim 17 wherein the system is further configured to operate in temporary mode of operation when at least one of: the inlet temperature and the outlet temperature are outside a predetermined range.

20. The system of claim 19 wherein the temporary mode operation comprises: calculating first and second control terms and accelerating the change of the modified integral term by multiplying a measured temperature error by a weighting factor and adding it to the integral sum, and setting the modified derivative term to zero when the outlet and/or inlet temperatures begin moving toward the predetermined range, and resuming normal operations when the outlet and/or inlet temperatures are within the predetermined ranges.

21. A patient temperature control system comprising:
- at least one heat exchange device configured to affect temperature of circulating in response to receipt of a power signal;
- a circulating pump for circulating fluid through said at least one heat exchange device and at least one interconnectable contact pad;
- an inlet temperature sensor which monitors the fluid temperature circulating out of the at least one interconnectable pad and an outlet sensor which measures the fluid temperature circulating into the at least one interconnectable pad; and
- a controller connectable to the at least one heat exchange device and the inlet and outlet temperature sensors, said controller configured to identify a first control term proportional to a first difference in temperature between the inlet temperature and a selected set point, and a second control term proportional to a difference between the outlet temperature and a selected set point, wherein the first and second control terms are further employed by the system controller to generate a power signal transmittable to at least one heat exchange device configured to affect the temperature of the circulating fluid.

22. The system of claim 21 wherein the controller is further connectable to at least one of: a first heat exchange device configured for heating a fluid and a second heat exchange device configured for cooling the circulating fluid, wherein the power signal is selectively transmittable to either the first or second heat exchange device.

23. The system of claim 22 including at least one auxiliary pump configured for pumping said fluid through at least one of the first and second heat exchange device to effect heat exchange between a medium located in each of the first and second heat exchange device and the fluid.

24. The system of claim 21 wherein the power signal is transmittable to at least one auxiliary pump for controlling the speed of the auxiliary pump.

25. The system of claim 21 wherein the controller is further connectable to a user interface through which user instructions may be entered regarding the temperature set point.

26. The system of claim 21 wherein the first control term may be determined from: Gain×(Measured Flow Rate−Flow Offset)×(Fluid Temperature Set Point−Measured Inlet Temperature).

27. The system of claim 26 wherein the system controller is further configured to include a second control term which is calculated using a PID controller which further includes a modified integral term; modified derivative term and a variable gain.

28. The system of claim 27 wherein the second control term is calculable by the following:

$$\text{second control term} = \text{Variable Gain} \times (K_p \times \text{Error} + K_i \times (\text{Modified Integral (Error)})) + K_d \times (\text{Modified Derivative (Error)})$$

where:

Variable Gain=$K_0+K_1\times$Measured Flow Rate.

29. The system of claim 28 wherein the modified integral term is configured to reduce overshoot and oscillation in the control system by using a rate of change of a measured temperature error to determine when to add the measured temperature error to an integral sum relating to the (Modified Integral (Error)).

30. The system of claim 29 wherein the modified derivative term is calculated using a least squares fit for N number of measured temperature errors.

31. The system of claim 29 wherein the system is further configured to operate in temporary mode of operation when at least one of: the inlet temperature and the outlet temperature are outside a predetermined range.

32. The system of claim 31 wherein the temporary mode operation comprises: calculating first and second control terms and accelerating the change of the modified integral term by multiplying the measured temperature error by a weighting factor and adding it to an integral sum, setting the modified derivative term to zero when the outlet and/or inlet temperatures begin moving toward the predetermined range, and resuming normal operations when the outlet and/or inlet temperatures are within the predetermined range.

* * * * *

UNITED STATES PATENT AND TRADEMARK OFFICE
CERTIFICATE OF CORRECTION

PATENT NO.    : 6,818,012 B2
DATED         : November 16, 2004
INVENTOR(S)   : Ellingboe It is certified that error appears in the above-identified patent and that said Letters Patent is hereby corrected as shown below:

Column 2,
Line 27, after "control", delete ",";
Line 27, after "system", insert -- , --;
Line 28, delete "which";
Line 43, after "include", insert -- a --;
Line 45, delete "for fluid";
Line 46, after "and", insert -- a --;
Line 46, after "selected", insert -- temperature --;
Line 50, after "second", insert -- control --;
Line 65, after "circulating", insert -- fluid, e.g. --;
Line 65, after "water", insert -- , --.

Column 3,
Line 25, delete "value", and insert therefor -- values --;
Line 33, delete "modify", and insert therefor -- modified --.

Column 4,
Line 26, delete "temperatures", and insert therefor -- temperature(s) --.

Column 12,
Line 57, delete "setpoint", and insert therefor -- set point --;
Line 65, delete "temperature", and insert therefor -- Temperature --.

Column 13,
Line 2, delete "require", and insert therefor -- required --;
Line 42, delete "rate", and insert therefor -- rates --;
Line 64, delete "Gain", and insert therefor -- gain --.

Column 14,
Line 27, delete "delayed", and insert therefor -- delay --;
Line 41, delete "machine", and insert therefor -- system --.

Column 15,
Line 3, delete "internal", and insert therefor -- interval --;
Line 15, delete "$T_i^.$", and insert therefor -- $t_i$ --;
Line 15, delete "$T_1$", and insert therefor -- $T_i$ --;
Line 18, after "Bt", insert -- , --;
Line 20, delete "Is", and insert therefor -- is --;

Line 23, delete " $NN \left(\sum t_i^2\right) - \left(\sum t_i^2\right)$ ", and insert therefor -- $NN \left(\sum t_i^2\right) - \left(\sum t_i\right)^2$ --;

UNITED STATES PATENT AND TRADEMARK OFFICE
CERTIFICATE OF CORRECTION

PATENT NO. : 6,818,012 B2
DATED : November 16, 2004
INVENTOR(S) : Ellingboe

It is certified that error appears in the above-identified patent and that said Letters Patent is hereby corrected as shown below:

<u>Column 15 (cont'd),</u>

Line 26, delete " $N\left(\sum t_i^2\right) - \left(\sum t_i^2\right)$ ", and insert therefor -- $N\left(\sum t_i^2\right) - \left(\sum t_i\right)^2$ --;

Line 29, after "estimate", insert -- glet --;

Line 34, delete "Sum Temperature = $\sum_{i=h-n}^{\lambda} T_i$ ", and insert therefore -- Sum Temperature = $\sum_{i=h-n}^{h} T_i$ --;

Line 38, "Sum Time = $\sum_{i=h-n}^{\lambda} t_i$ ", and insert therefor -- Sum Time = $\sum_{i=h-n}^{h} t_i$ --;

Line 42, delete "Sum Time Temperature = $\sum_{i=h-N}^{\lambda} t_i T_i$ ", and insert therefor -- Sum Time Temperature = $\sum_{i=h-N}^{h} t_i T_i$ --;

Line 46, after "line", insert -- , then --;

Line 48, delete " $T_{h-n} = A = Bt_{h-n}$ ", and insert therefor -- $T_{h-n} = A + Bt_{h-n}$ --;

Line 50, after "set", insert -- : --;

Line 54, delete " $\sum_{i=h-N}^{h} t_i = \tau \sum_{i=o}^{h} i = 0+1+2...N-1 = Const$ ", and insert therefor -- $\sum_{i=h-N}^{h} t_i = \tau \sum_{i=o}^{h} i = 0+1+2...N-1 = Const$ --;

Line 58, delete " $\sum_{i=h-N}^{h} t_i T_i = T(0*T_{h-N} + 1*T_{h-n+1} + 2*T_{h-N+2} + ....(N-1)T_h)$ ", and insert therefor -- $\sum_{i=h-N}^{h} t_i T_i = \tau(0*T_{h-N} + 1*T_{h-N+1} + 2*T_{h-N+2} + ....(N-1)T_h)$ --;

UNITED STATES PATENT AND TRADEMARK OFFICE
CERTIFICATE OF CORRECTION

PATENT NO. : 6,818,012 B2  
DATED : November 16, 2004  
INVENTOR(S) : Ellingboe

It is certified that error appears in the above-identified patent and that said Letters Patent is hereby corrected as shown below:

Column 15 (cont'd),

Line 65, delete " $\sum_{i=h-N}^{h} T_i = \sum_{i=h-N-1}^{h-1} T_i - T_{h-N-1} + T_h$ ", and insert therefor -- $\sum_{i=h-N}^{h} T_i = \sum_{i=h-N-1}^{h-1} T_i - T_{h-N-1} + T_h + T_{h-N-1}$ --.

Column 16,
Line 2, after "then", insert -- : --;
Line 16, delete "Sum time = 45;    \*(0+1+2...9) not sum time", and insert therefor -- Sum Time = 45;    \*(0+1+2...9) --;
Line 17, delete "Sum time squared = 285;    *(1+4+9+...+8)", and insert therefor -- Sum Time Squared = 285; \*(1+4+9+...+81) --;
Line 18, delete "\* 10$^{-\text{num - samples}}$*sum time square – (sum - time)2", and insert therefor -- \*10$^{\text{num samples}}$*Sum Time Squared – (Sum - Time)2 --;
Line 19, delete "Tau = 1;", and insert therefor -- Tau $\tau$ = 1; --;
Line 20, delete "variable", and insert therefor -- variables --;
Line 21, delete "Sum time error    \*sum of time temperature error", and insert therefor -- Sum Time Error    \*sum of ten times temperature error --;
Line 22, delete "Sum error", and insert therefor -- Sum Error --;
Line 23, delete "Error intercept", and insert therefor -- Error Intercept --;
Line 24, delete "Error slope", and insert therefor -- Error Slope --;
Line 25, delete "Initially all variables are set to zero", and insert therefor -- Initialize all variables to zero (\*), and: --;
Line 26, delete "Sum time error = sum time error = $\tau$ * sum error +", and insert therefor -- Sum Time Error = Sum Time Error - $\tau$ * Sum Error + --;
Line 27, delete "Num sample * $\tau$ * error + error intercept", and insert therefor -- Num samples * $\tau$ * Error + Error Intercept --;
Line 28, delete "Error intercept = (sum time square * sum error -", and insert therefor -- Error Intercept = (Sum Time Square * Sum Error --;
Line 29, delete "sum time * sum time error) / Delta;", and insert therefor -- Sum Time * Sum Time Error) / Delta --;
Line 30, delete "Error slope = (num samples * sum time error – sum time * sum error)", and insert therefor -- Error Slope = (Num Samples * Sum Time Error – Sum Time * Sum Error) --;
Line 31, delete "/Delta;", and insert therefor -- /Delta. --.

UNITED STATES PATENT AND TRADEMARK OFFICE
CERTIFICATE OF CORRECTION

PATENT NO. : 6,818,012 B2
DATED : November 16, 2004
INVENTOR(S) : Ellingboe

It is certified that error appears in the above-identified patent and that said Letters Patent is hereby corrected as shown below:

Column 23,
Line 25, delete "ranges", and insert therefor -- range --;
Line 51, delete "devices", and insert therefor -- device --.

Column 24,
Line 29, delete "ranges", and insert therefor -- range --;
Line 39, after "outlet", insert -- temperature --.

Signed and Sealed this

Fifteenth Day of November, 2005

JON W. DUDAS
*Director of the United States Patent and Trademark Office*